United States Patent
Yamakawa et al.

(10) Patent No.: US 11,331,068 B2
(45) Date of Patent: May 17, 2022

(54) X-RAY DEVICE, X-RAY INSPECTION METHOD, AND DATA PROCESSING APPARATUS

(71) Applicant: JOB CORPORATION, Kanagawa (JP)

(72) Inventors: Tsutomu Yamakawa, Kanagawa (JP); Shuichiro Yamamoto, Kanagawa (JP)

(73) Assignee: JOB Corporation, Kanagawa (JP)

( * ) Notice: Subject to any disclaimer, the term of this patent is extended or adjusted under 35 U.S.C. 154(b) by 167 days.

(21) Appl. No.: 16/623,552

(22) PCT Filed: Jun. 19, 2018

(86) PCT No.: PCT/JP2018/023322
§ 371 (c)(1),
(2) Date: Dec. 17, 2019

(87) PCT Pub. No.: WO2018/235823
PCT Pub. Date: Dec. 27, 2018

(65) Prior Publication Data
US 2020/0138398 A1 May 7, 2020

(30) Foreign Application Priority Data

Jun. 20, 2017 (JP) .............................. JP2017-120433

(51) Int. Cl.
*A61B 6/00* (2006.01)
*G01N 23/04* (2018.01)
*G01N 23/083* (2018.01)

(52) U.S. Cl.
CPC ............. *A61B 6/584* (2013.01); *G01N 23/04* (2013.01); *G01N 23/083* (2013.01); *G01N 2223/618* (2013.01)

(58) Field of Classification Search
CPC .......... A61B 6/584; A61B 6/00; G01N 23/04; G01N 23/083; G01N 2223/618; G01N 2223/423; G01N 23/087; G01N 23/18
(Continued)

(56) References Cited

U.S. PATENT DOCUMENTS

2009/0262997 A1  10/2009  Zou et al.
2016/0206269 A1  7/2016  Jung et al.
2018/0214113 A1*  8/2018  Yamakawa .......... G01N 23/087

FOREIGN PATENT DOCUMENTS

JP    2002-152593    5/2002
JP    2002-152594 A    5/2002
(Continued)

OTHER PUBLICATIONS

Extended European search report dated Mar. 11, 2021 issued in the corresponding EP Patent Application No. 18821561.0.
(Continued)

*Primary Examiner* — David P Porta
*Assistant Examiner* — Gisselle M Gutierrez
(74) *Attorney, Agent, or Firm* — Carrier Blackman & Associates, P.C.; Joseph P. Carrier; Jeffrey T. Gedeon

(57) ABSTRACT

In an X-ray inspection, a detection unit with a detector is provided. The detection unit detects transmitted amounts of the X-rays generated by an X-ray generator and transmitted through the object in each of n-number X-ray energy bins (n is a positive integer of 2 or more) which are set in advance to the X-rays, and outputs detection signals corresponding to the transmitted amounts. An information acquisition unit acquires, based on the detection signal, information showing a thickness t of the object and an average linear attenuation coefficient μ in a transmission direction of fluxes of the X-rays, in each of the energy bins. A pixel data calculation unit calculates, based on the acquired information, pixel data
(Continued)

composed of pixel values each obtained by multiplying addition information by the thickness t. Addition information is obtained by mutual addition of the average linear attenuation coefficients $\mu$ in the respective energy bins.

20 Claims, 22 Drawing Sheets

(58) Field of Classification Search
USPC .......................................................... 378/62
See application file for complete search history.

(56) References Cited

FOREIGN PATENT DOCUMENTS

| | | |
|---|---|---|
| JP | 2008-229122 | 10/2008 |
| JP | 2009-261942 A | 11/2009 |
| JP | 2010-091483 | 4/2010 |
| JP | 2011-196753 | 10/2011 |
| WO | 2016/171186 | 10/2016 |
| WO | 2017/069286 | 4/2017 |

OTHER PUBLICATIONS

H. Watabiki et al., "Development of Dual-Energy X-Ray Inspection System", Anritsu Technical, No. 87, Mar. 2012.

* cited by examiner

FIG.6
(A)
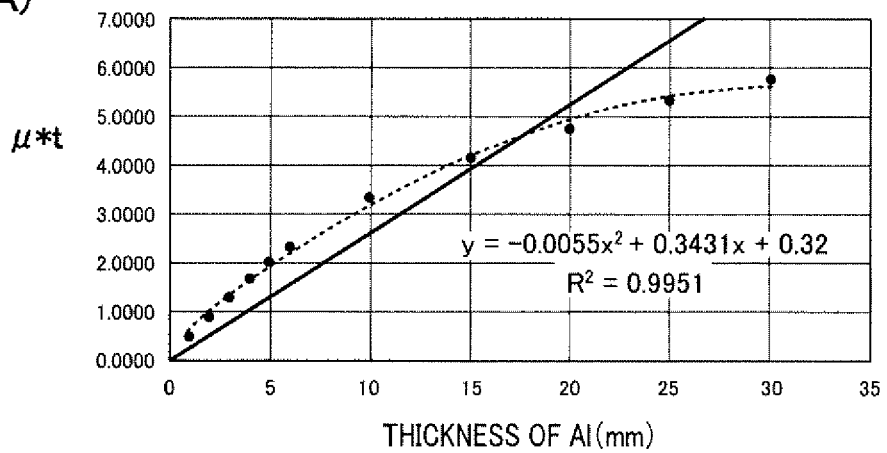
[ THICKNESS OF Al vs $\mu_1 * t$ ]
$y = -0.0055x^2 + 0.3431x + 0.32$
$R^2 = 0.9951$
(B)
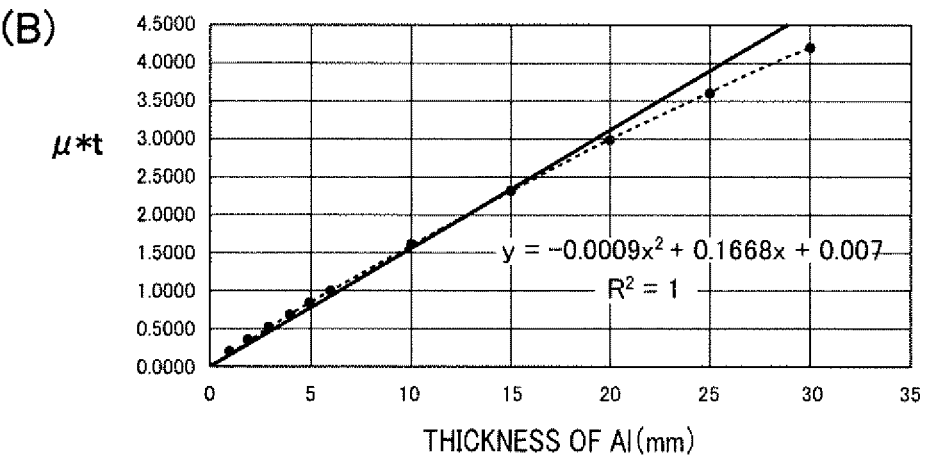
[ THICKNESS OF Al vs $\mu_2 * t$ ]
$y = -0.0009x^2 + 0.1668x + 0.007$
$R^2 = 1$
(C)
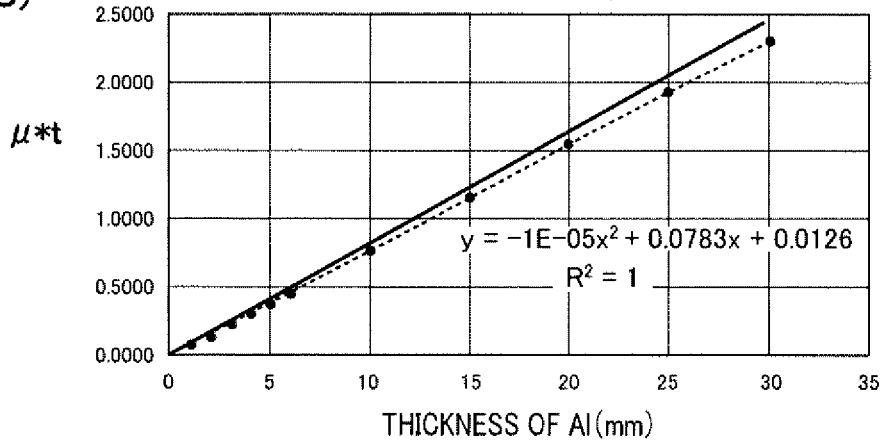
[ THICKNESS OF Al vs $\mu_3 * t$ ]
$y = -1E-05x^2 + 0.0783x + 0.0126$
$R^2 = 1$

[THREE-DIMENSIONAL SCATTER DIAGRAM]

[ABSORPTION VECTOR LENGTH IMAGE]

[AVERAGE ABSORPTION VALUE IMAGE]

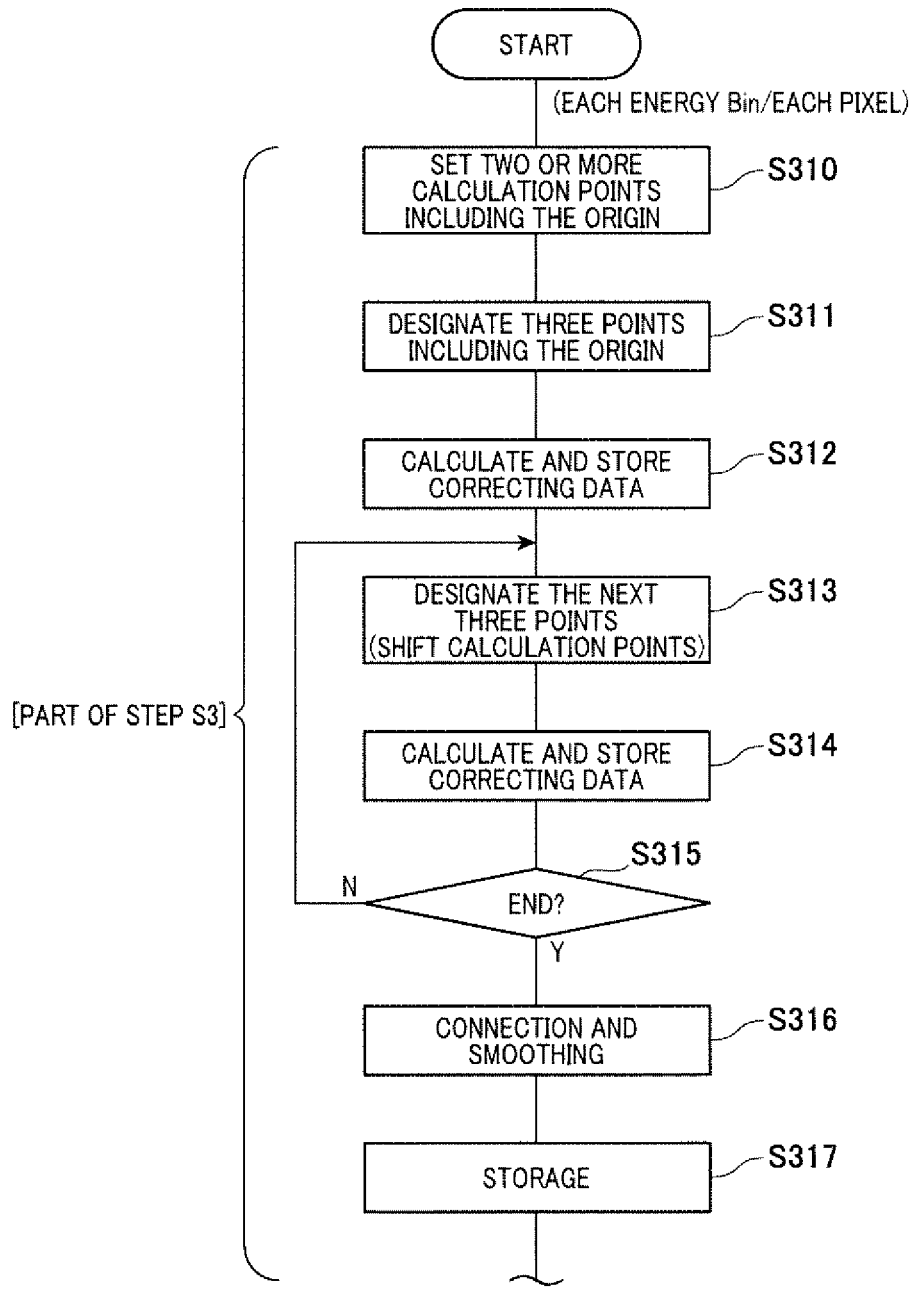

X-RAY DEVICE, X-RAY INSPECTION METHOD, AND DATA PROCESSING APPARATUS

CROSS-REFERENCE TO RELATED APPLICATION

This application is based on and claims the benefit of priority from earlier Japanese Patent Application No. 2017-120433 filed on Jun. 20, 2017, the description of which is incorporated herein by reference.

TECHNICAL FIELD

The present invention relates to an X-ray device, an X-ray inspection method, and a data processing apparatus which scan an object with X-rays to acquire X-ray transmission data and inspect the object based on the acquired data, and in particular, to the X-ray device, the X-ray inspection method, and the data processing apparatus which focus on differences in respective X-ray transmission characteristics provided by a plurality of energy ranges (i.e., energy bins) set on the X-ray energy spectrum.

BACKGROUND ART

In recent years, inspection using X-ray beams to check the internal state of an object has been widely used in various fields, such as foreign matter inspection of food, baggage inspection, and medical X-ray mammography.

For example, airports, public facilities, or the like use a content inspection that is an inspection of the types and shapes of baggage or mail contents, which is carried out without opening the baggage or mail. It is desired that such a content inspection should find out the presence of foreign matters (for example, metal pieces), if mingled into known types of objects (for example, food such as bread), and specify the types of the foreign matters. In other words, there is a potentially higher need for determining the types and/or shapes of objects (materials) by using X-rays.

For such needs, for example, there is proposed a technique as set forth in a patent publication 1 (JP-A-2010-091483, title of the invention is a "method and apparatus for inspecting foreign matters"). This patent publication 1 is based on an inspection technique called a dual energy technique (or a subtraction technique). This inspection technique uses the fact that two types of X-rays of energy (that is, two types of X-rays having different wavelengths) penetrating a substance arises a difference therebetween in X-ray transmission information. Practically, this inspection technique uses the following processing. First, two types of X-ray images based on lower X-ray energy and higher X-ray energy are made simultaneously, and a difference between the images is calculated. Then, from the resultant image difference, image components of a mingled foreign matter are extracted. The image components are then subjected to threshold processing to detect the foreign matter.

In the patent publication 1, optimum parameters for the difference calculation are set automatically, in addition to performing the foregoing basic process, to detect foreign maters at higher sensitivity. The patent publication 1 suggests use of a detector capable of detecting incidence of X-ray photons, with X-ray photon energy being discriminated. In other words, as a measure to simultaneously obtain two types of X-rays having lower energy and higher energy, the patent publication 1 suggests use of a well-known photon-counting X-ray radiation and detection system.

There is known another inspection method based on the foregoing dual energy technique as described in a non-patent publication 1. This non-patent publication 1 provides a detecting system using a basic configuration for the dual energy technique. With this configuration, an overlap of objects on the conveyance belt is ensured not to be mistakenly taken as foreign matters, so that foreign matters are detected with higher sensitivity.

When using the dual energy technique described in the patent publication 1 and the non-patent publication 1, an object or foreign matters mingled into the object may be detected with sensitivity that is improved to some extent. The term "improved to some extent" means that the detection sensitivity is improved if imaging conditions and/or image processing conditions are narrowed to specific conditions. Thus, detection conducted under such specific conditions limits imaging objects or imaging conditions to which the technique is applied, that is, narrows the conditions for detecting foreign matters.

Specifically, the dual energy technique described in these publications offers accuracy that is so low as not to reflect the difference in attenuation degree of the X-ray photon energy and materials, and gives little consideration to the electric noise or nonlinear characteristics of X-ray detection circuits, which may be unignorable problems.

CITATION LIST

Patent References

[Patent Publication 1] JP-A-2010-091483
[Non-Patent Publication 1]
"Development of dual-energy X-ray foreign matter detector", No. 87, March 2012, Anritsu Technical

SUMMARY OF THE INVENTION

Technical Problem

By the way, in X-ray dental applications such as an X-ray panoramic imaging device, the X-ray beams pass through hard tissues such as teeth and/or jaws. The X-ray beams which have entered such objects are subjected to beam hardening (beam hardening phenomenon), whereby a detected X-ray spectrum is shifted relatively to a higher energy side thereof. In other words, due to the beam hardening, the quantity of X-rays (the number of X-ray photons) in a lower energy side is reduced, thereby being influenced more hardly by noise.

In addition, influence of the beam hardening will also appear such that the effective (average) energy amounts of the respective X-ray energy ranges depend on object thicknesses. Particularly, as the X-ray energy range shifts toward its lower energy side in the X-ray spectrum, fluctuations occurring due to differences among object thickness become prominent, thereby reducing quantitative quality of reconstructed images.

With consideration of such drawbacks, an object of the present invention is to reduce the influence of the beam hardening on the attenuation of the X-ray beams, obtain a reduction of image noise and improved image contrast, and secure more quantitative inspection performance as to differences of object thicknesses in the X-ray paths when an X-ray inspection of objects is performed.

Solution to the Problems

With consideration of the forgoing situation, one mode of the present invention provides an X-ray device which inspects an object, wherein beam-shaped X-rays are radiated to the object and the object is inspected based on amounts of the X-rays transmitted through the object. This device is characterized in that the device includes:

X-ray generating means that generates the X-rays;

X-ray detecting means that detects transmitted amounts of the X-rays generated by the X-ray generating means and transmitted through the object in each of n-number X-ray energy bins (n is a positive integer of 2 or more) which are set in advance to the X-rays, and outputs detection signals corresponding to the transmitted amounts;

information acquiring means that acquires, based on the detection signals detected by X-ray detecting means, information showing a thickness t of the object and an average linear attenuation coefficient $\mu$ in a transmission direction of fluxes of the X-rays, in each of the energy bins; and pixel data calculating means that calculates pixel data composed of pixel values each obtained by multiplying addition information by the thickness t, based on the information acquired by the information acquiring means, the addition information being obtained by mutual addition of the average linear attenuation coefficients $\mu$ in the respective energy bins.

Practically, the X-ray device is for example an in-line X-ray foreign matter inspection apparatus, a substance identifying apparatus for identifying (estimating or evaluating) the type and/or property of an object (or compositions thereof) using X-rays, a medical apparatus for X-ray mammography, or a dental X-ray diagnostic apparatus for diagnosing states of tooth rows and/or gums. The "object" is, for example, an object itself to be X-ray inspected or foreign matter which is present in an object. For medial X-ray devices, the "object" is the breast, oral cavity, or limb, which is parts of a human or animal body.

Further, the energy ranges of the X-rays are defined as partial energy ranges which are set to a continuous energy spectrum of the X-rays (i.e., polychromatic X-rays). In the present invention, the energy ranges are previously set as n-number energy ranges (n is a positive integer of two or more). For example, in a case where the X-rays are detected in photon-counting measurement under the "n"=3, the energy ranges are set as a lower energy range of 18 to 23 key, an intermediate energy range of 23 to 38 keV, and a higher energy range of 38 to 50 keV. When the X-ray detection is carried out under the dual energy method (normally n=2), the energy ranges are set as a lower energy range of 18 to 23 keV and a higher energy range of 38 to 50 keV. The energy range is also referred to as energy bins.

Incidentally the foregoing information acquisition and image data calculation can be performed every energy range (bin) and every pixel or every pixel area consisting of two or more pixels. In addition, the acquisition of characteristics and calculation of correcting data can be applied to a detection signal outputted from a detector (or sensor) having a single pixel or outputted form an X-ray spectrometer.

Effect of the Invention

In the present invention, the image data calculating means calculates image data composed of pixel values which are multiplied values of addition information by a thickness t taken along an X-ray path in an object. The addition information is obtained by mutual addition of the average linear attenuation coefficients $\mu$ in the respective energy ranges (bins). The beam hardening will cause an X-ray amount (i.e., the number of X-ray photons) in the lower energy ranges to decrease, thereby relatively increasing noise component. However, the image data calculated in the present invention suppress the noise components from increasing relatively to signals, compared to a method of calculating the image data based on the square of the linear attenuation coefficient $\mu$. In addition, an effective energy amount in the lower energy ranges increase relatively, so that the liner attenuation coefficient $\mu$ becomes smaller. However, since there can be provided larger contribution of a relative noise reduction, a CNR (contrast to noise ratio) can be improved without lowering the image contrast, so that the conventional image contrast is maintained.

Moreover, the pixel values are calculated by being multiplied by the thickness t, thereby representing a quantitative performance to the thickness t. From these points of view, the X-ray inspection can be conducted such that influence of the beam hardening on the X-ray attenuation is reduced, nose in the images is suppressed from increasing and a higher image contrast is provided, thus securing a quantitate analysis based on an object thickness in an X-ray path direction.

BRIEF DESCRIPTION OF DRAWINGS

In the accompanying drawings:

FIG. 6 exemplifies simulated graphs, for each of the X-ray energy bins, which explain a relationship between thicknesses t and X-ray attenuation amounts $\mu t$, which show influence of the beam hardening and other factors about aluminum material;

FIG. 22 is a partial flowchart explaining a part of processes performed by the processor, according to the fifth modification.

DESCRIPTION OF EMBODIMENTS

Hereinafter, embodiments according to the present invention will now be described. A data processing apparatus according to the present invention is also installed in this X-ray device in a functionally integrated manner.

[First Embodiment]

Referring to FIG. 1 to FIG. 15, a first embodiment of the X-ray device (and the data processing apparatus) will now be described.

Figure 1:
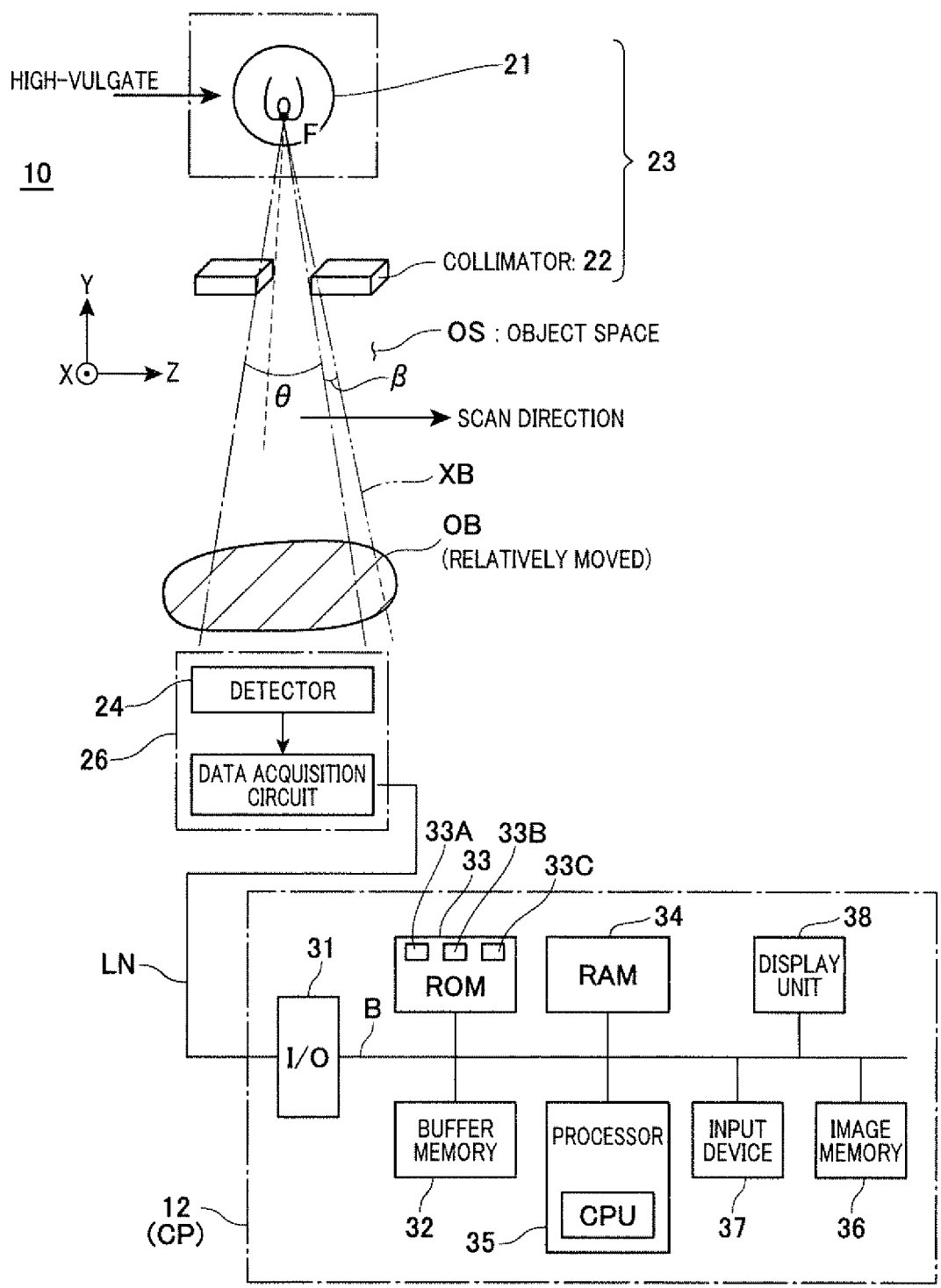
FIG. 1 is a block diagram outlining the configuration of an X-ray device according to an embodiment of the present invention.

FIG. 1 outlines the X-ray device provided according to the first embodiment. This X-ray device can be provided as apparatuses for X-ray foreign-matter inspection or X-ray mammography. These apparatuses are directed to acquiring tomographic images and/or projected images of an object being inspected. In particular, the apparatuses can also be directed to inspecting whether or not foreign matter is attached to or misplaced inside an object (for example, a food item) and/or identifying (estimating, determining) the type and/or property of the foreign matter. The foreign matter is a substance other than materials composing a non-contained normal object. Such substances are metal pieces such as aluminum pieces or insects such as cockroaches. An apparatus to check existence of foreign matter is known as an X-ray foreign matter inspecting apparatus. The X-ray device of this embodiment is intended to perform an inspection to identify the type or property (or physical state) of foreign matter, that is, material (substance) identification, if there is known existence of the foreign matter.

FIG. 1 shows an X-ray device 10 provided with a basic configuration required by the foregoing various substance identifying apparatuses (including an X-ray mammographic apparatus to check the breast as to whether or not a lesion is present).

As shown in FIG. 1, the X-ray device 10 includes, as its essential elements, an X-ray generator 23 equipped with an X-ray tube 21 generating X-rays having a continuous energy spectrum and a photon counting detector 24 counting the number of photons and being arranged to be opposed to the ray tube 21.

Although the present embodiment exemplifies, as the above, the X-ray device provided with an X-ray generating apparatus which generates X-rays having a continuous spectrum and a photon counting detector, the X-ray device according to the present invention will not be limited such a configuration. Another configuration which can be applied to the X-ray device is to have an X-ray generating apparatus and a detector which are dedicated to, what is called, dual-energy X-ray radiation and detection. In this configuration, the detector is configured to integrate incident X-ray photons during a specified duration in order to output a signal corresponding each of the integrated values.

Returning to FIG. 1, a driving high-voltage is supplied to the X-ray tube 21 from a not-shown X-ray high-voltage generator for X-ray radiation. A space OS (i.e., object space) is provided between the X-ray tube 21 and the detector 24 and an object OB being inspected (or inspected object) is positioned in the space OS. For inspecting the object OB, the pair of the X-ray tube 21 and the detector 24 and the object OB are relatively moved to each other.

In an X-ray inspection apparatus to inspect the type or property of a substance included in an object being inspected, the object OB is an object itself. In this case, by way of example, the object OB is a human breast, so that a mammographic X-ray imaging is conducted. Another example of the X-ray inspection apparatus can be provided as a dental panoramic imaging apparatus, in which the object OB is the jaw of a human body or an animal.

Figure 2:
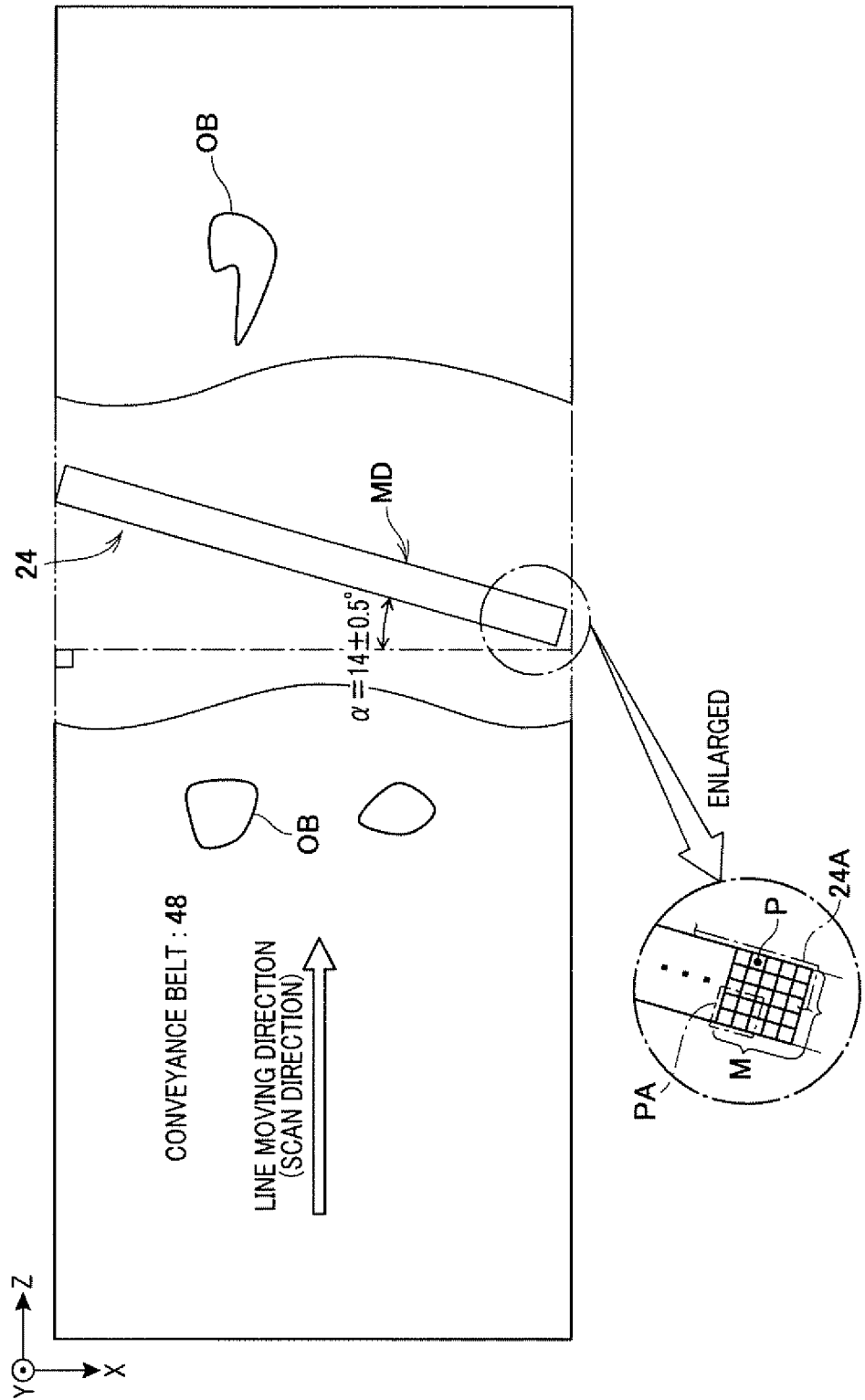
FIG. 2 is an illustration explaining a detector obliquely arranged in the X-ray device according to the embodiment.

Further, for example, in an X-ray foreign-matter inspection which inspects a foreign matter which may be present in (or outside, as attached thereon) an object (such as a food item or an industrial product whose component types are known), the object OB is placed on a conveyance belt 48 so as to pass through the object space OS (refer to FIG. 2). Alternatively, it is possible to configure such that the object OB is located fixedly but the pair of the X-ray tube 21 and the detector 24 is moved around the object OB.

The X-ray tube 21 has a tube focal point F whose focal radius is 0.5 mmφ, for instance. Hence, the tube focal point F can be regarded as a substantial spot-shaped X-ray source. The X-rays emitted from the X-ray tube 21 are shaped, via a collimator 22, into a cone beam (or a fan beam) of X-rays. In FIG. 1, a cone-beam shaped X-rays XB is shown which has a cone angle θ and a fan angle β. In the configuration shown in FIG. 1, a Cartesian coordinate system with XYZ axes is provided, in which the Z-axis reaction is defined as a direction along which an object OB is moved in the object space OS, which is thus referred to as a scan direction. The emitted X-rays XB are spread in a cone beam in the Y-axis direction which is along the height direction.

The cone-beam X-ray beam XB is transmitted through the object OB during which the beam is attenuated in its intensity, and the transmitted X-rays hits the detector 24. In the X-ray mammography, the pair of the X-ray generating apparatus equipped with the X-ray tube 21 and the detector 24 is rotated around a human breast compressed by compression plates in a predetermined angular range.

Incidentally, in the case where the photon counting detector 24 is adopted as explained in the present embodiment, the X-ray tube 21 radiates continuous-spectrum X-rays. In contrast, if the system adopts an integration type of detector, the X-ray tube is configured to radiate X-rays of dual-energy spectrums. In this case, two X-rays tubes radiating X-rays of mutually different energy ranges can be provided, or a system configuration having a single X-ray tube can also be provided. In the latter case, the single X-ray tube radiate a continuous spectrum of X-rays which can be divided into two energy ranges using for example X-ray filters (for example, refer to the foregoing non-patent publication 1).

Returning to FIG. 1, the detector 24 has an elongated shape in which a plurality of modules M (for example, 29 modules) arranged in sequence, as shown in FIG. 2. In each module M, pixels P are two-dimensionally mapped in a matrix, such as 80×20 pixels, each having a pixel size of 0.2 mm×0.2 mm, for example. With this configuration, the foregoing X-ray incident window MD, which is approx. 47 cm in the longitudinal size and 0.4 cm in the lateral size, is formed as a detection layer 24A. The X-ray incident window MD provides 20×2348 pixels, for example. The plurality of modules M are aligned linearly, but in terms of pixel mapping, the detector 24 is configured as a direct conversion type of X-ray detector with an elongated shape, in which a plurality of pixels P exist even in the lateral direction. In the present embodiment, as will be detailed later, there is a configuration for correcting measured counts influenced by physical phenomena such as beam hardening. This correction can be performed for each of the pixels P as well as each imaginary area imaginarily formed by grouping adjacently positioned actual pixels P. This imaginary area is exemplified by a pixel area PA shown in FIG. 2.

Under the conveyance belt 48, this detector 24 is arranged obliquely such that the longitudinal axis of the detector is skewed by a predetermined angle (e.g., approximately 14 degrees) in the scan direction of the object OB (or a direction perpendicular to the scan direction).

Each of the module M has the detection layer 24A made of a semiconductor material, such as CdTe or CZT, which serves as an X-ray detecting element converting directly from X-rays to electrical signals. Though not shown, on both sides of the detection layer 24A, charging and collecting electrodes are arranged for applying a high-voltage bias voltage between the electrodes.

Figure 3:
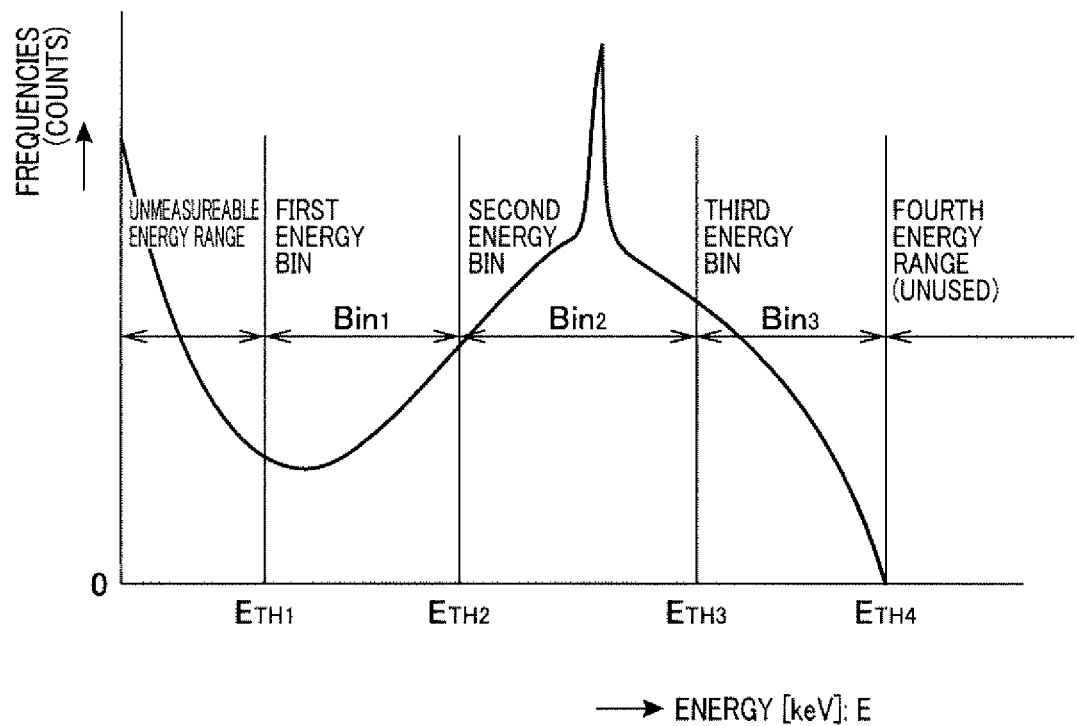
FIG. 3 is a graph explaining a spectrum of incidence of X-ray photons, in which a plurality of energy bins are set in the spectrum.

This detector 24 is a photon counting detector (a photon counting type of detector), which regards X-rays as an aggregation of photons having various energies and is capable of detecting and measuring the number of photons of each of the X-ray every bins (X-ray energy ranges). As shown in FIG. 3, the X-ray energy bins are set for example as three energy bins $Bin_1$ to $Bin_3$ (respectively corresponding to a lower X-ray energy range, a middle X-ray energy range, and a higher X-ray energy range). The number of energy ranges is not limited to three, but may be one, or two or more which is other than three. In the energy spectrum [key], an energy range lower than a lower-limit threshold TH1 and an energy range upper than an upper-limit threshold TH4 (which is set to the tube voltage) are set as being an unmeasurable range and an unused range, respectively. A range between the thresholds TH1 to TH4 is divided into a single range (in this case, the thresholds are composed of only TH1 and TH4) or into a plurality of energy bins, BINs. For example, when thresholds TH2 and TH3 are set as shown in FIG. 3, there can be provided three energy bins, BINs.

In the detector 24, a layered data acquisition circuit 25 is formed, as an ASIC layer, beneath the detection layer 24A. With this formation, every pixel P and every energy bin, BIN, X-ray intensities are detected by the data acquisition circuit 25 as digital counts (accumulated values) indicating the number of photons measured at intervals. The detector 24 and the data acquisition circuit 25 configure a detection unit 26.

When a single photon hits a single pixel P, an electrical pulse signal is generated at the pixel P, of which signal wave height depends on the energy of the photon. The wave height value of the electrical pulse signal, that is, the energy amount, thus makes the count by one in an energy bin, BIN, to which the energy amount belongs. The count is thus collected by the data acquisition circuit 25, at every pixel P and in every energy bin, BIN, as accumulated values (digital values) measured at intervals.

By setting a sampling frequency to a higher value in the data acquisition circuit 25, the digital counts can be acquired from the respective ones of, for example, 20×2348 pixels at a frame rate of, for example, 6600 fps, at every pixel P and in every energy bin, BIN This direct conversion type of detector, together with the data acquisition circuit, is known and, for example, exemplified by a European patent publication No. 2674787.

The detector 24 is not always limited to the foregoing direct-conversion type configuration. One alternative to this detector 24 is a photon counting detector configured as a $CeLaCl_3$ detector, in which SiPM (or also referred to as MPPC) is provided with micro columnar scintillators each of which has a diameter of several tens of micrometers.

The digital counts, which are repeatedly outputted at constant intervals from the data acquisition circuit 25 of the detection unit 26 at every pixel and in every energy bin, BIN, are sent as frame data to the next-stage data processing apparatus 12 via a communication line LN.

The data processing apparatus 12 can be installed as an apparatus integrated with the X-ray device 10 or an inspection system. As in the present embodiment, the data processing apparatus 12 can be communicably connected to the X-ray device 10 via the communication line LN. In this configuration, the line may be always-on connection or on-demand connection. In addition, the data processing apparatus 12 can be provided as a stand-alone type apparatus.

The data processing apparatus 12 is configured, by way of example, as a computer system CP. This computer system CP itself may be a computer system having known calculation functions, in which an interface (I/O) 31 is provided which is connected to the detection unit 26 via the communication line LN. To the interface 41, via internal buses B, a data processor 35 equipped with a buffer memory 32, a ROM (read-only memory) 33 (which foundations as a non-transitory computer readable medium), a RAM (random access memory) 34, and a CPU (central processing unit); an image memory 36; an input device 37; and a display unit 38 are communicably connected with each other via the buses.

The ROM 33 is provided to previously store therein computer-readable programs for correcting counts and identifying substances (materials), which enable the data processor 35 to read the programs and store them in its work area for execution of the programs. For this purpose, the ROM 33 is provided with a program storage area (functioning as a non-transitory computer recording medium) for previous storage of such programs. The ROM 33 is also provided with first and second data storage areas 338 and 33C (the first and second storage means) which stores therein data for correcting counts, i.e., calibration of the counts, which will be detailed later.

The processor 35 reads necessary programs from the program storage area 33A of the ROM 33 into its own work area. The processor 35 is a CPU dedicated to image processing. The buffer memory 32 is provided to temporarily memorize the frame data sent from the detection unit 26. The RAM 34 is provided to temporarily memorize data required during processing of the processor 35.

The image memory 36 is provided to store therein various image data and various kinds of information processed by the processor 35. The input device 37 and the display unit 38 function as a man-machine interface with users, in which the input device 37 receives input information given by users and the display unit 38 presents images and other information under control of the data processor 35.

<Correction Process>

A correction process for photon counts (measured amounts) performed in a system, which involves radiation of X-rays having a continuous energy spectrum and X-ray detection based on photon counting detection, will now be described. The correction process is executed by the processor 35.

First of all, the background of this correction for the counts will be described.

In recent years, there have been proposed many requests for identifying the type or shape of an object by using X-rays having a continuous energy spectrum. One such example, which can be seen in ensuring food safety, is an inspection of food items for checking whether the food items are contaminated with foreign matters The reason why the continuous-spectrum (polychromatic) X-rays are used in the present embodiment exists in the fact that it is difficult to realize such an inspection system which uses monochromatic X-rays, that is, X-rays having a particular energy, even though the monochromatic X-rays provide higher quantitative images and are controlled more easily if being possible to be realized. An apparatus for generating monochromatic X-rays needs an accelerator such as a synchrotron, so that usage of such an apparatus is limited in terms of various factors including higher cost, complex mounting, and output power.

In contrast, the continuous energy-spectrum X-rays are (i.e., polychromatic X-rays) can be generated by accelerating electrons with a higher voltage to be radiated to a target member, made of material such as tungsten or molybdenum, in the vacuum. That is, compared with generating the monochromatic X-rays, the polychromatic X-rays can be generated at overwhelmingly lower cost and in an easier mounting structure. However, it is true that imaging using such X-rays having a continuous energy spectrum sacrifices, more or less, a higher quantitative performance.

In particular, such a sacrifice is image quality. One of the factors greatly influencing the image quality is a beam hardening phenomenon (simply, referred to as beam hardening). The beam hardening is a phenomenon in which, in the event, an average (effective) energy amount is shifted to a higher energy side due tot the fact that, when the continuous energy X-rays pass through a substance, X-rays having lower energies are absorbed in the substance more than X-rays having higher energies. When this beam hardening occurs, artifacts are generated in reconstructed images or pixel values of such images tend to deteriorate their quantitative performance. More or less, the beam hardening depends on the depth of a substance in its degree (showing a larger amount of the beam hardening as the depth increases). It can be summarized such that the degree of the beam hardening results from differences in mutual interaction caused between molecules (atomics) of an object and X-ray phonons. Incidentally, factors influencing image quality by such physical phenomena include a heel effect resulting from an X-ray generator, besides the beam hardening phenomenon. The correction of counts in the present invention features alleviation of such influences caused due to the various physical phenomena once for all.

In addition, the correction of counts also contributes to correction of errors of the counts which are attributed to individual differences of circuits components and circuit substrates. Such errors include variations in gains of the respective circuits, variations of offsets, variations in linearity characteristics of respective circuits, and variations in charge sharing. It is general that these variations may be obstacles to higher-accurate data process (such as substance identification), but can be improved in the present embodiment.

The present inventors found that the beam hardening has influence depending on amounts of energy of the X-rays even within the range of each of the energy bins, BIN, to which an attention has not been paid so far. In order to improve this issue, a correction technique has been developed and provided by the inventors. Provided that the physical phenomenon is inherent to a substance, which is an object, and an apparatus being used, this correction technique can be regarded as a kind of calibration technique. From this point of view, data for the correction can be referred to as calibration data.

<Outline of Correction>

When the X-ray device according to the present embodiment is exemplified as an X-ray foreign-matter inspection apparatus, it is usual that an object being inspected (for example, a food item such as peppers) can be regarded as being composed of known substances (for example, its major component is water). Moreover, in such an inspection, a foreign matter being inspected is also limited to, for example, a particular metal preciously set (for example, one or more types of metals including aluminum, glass, iron, and/or other materials). In consideration of this situation, the correction technique for counts in the present invention is performed for previously acquired correction data assigned to various known substances. The X-ray device of the present invention thus provides a basic configuration for accomplishing processes necessary for the correction, which can be summarized below in the X-ray device according to the present embodiment.

Figure 4:
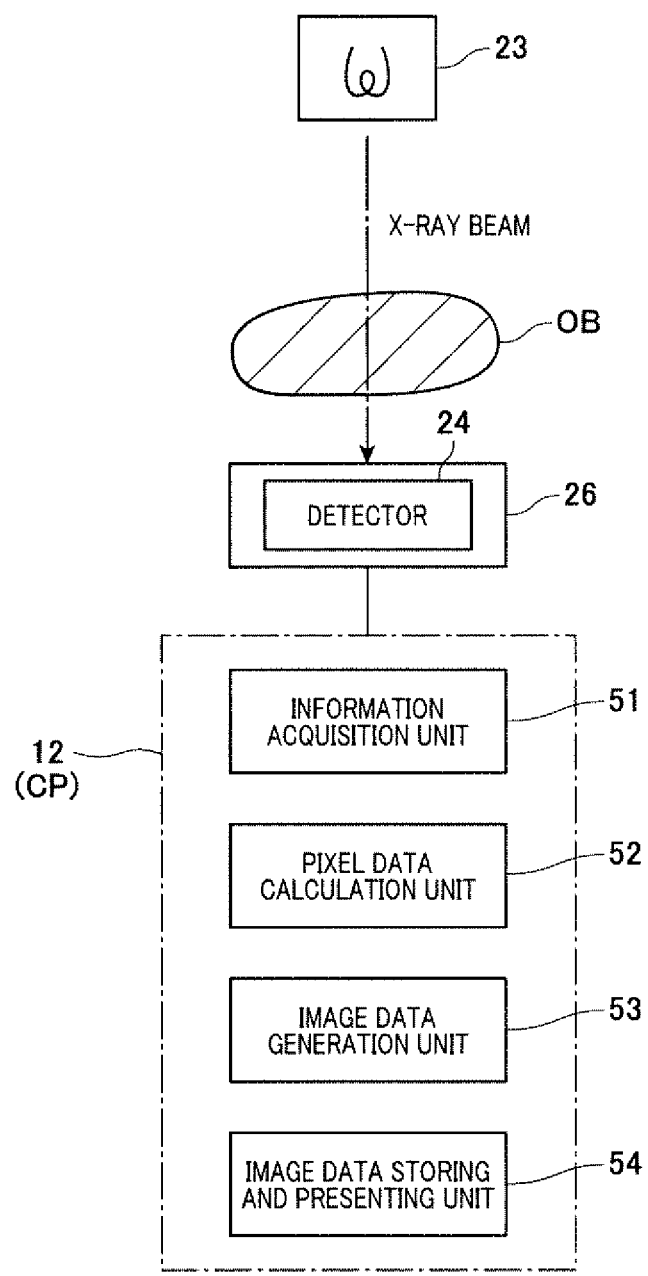
FIG. 4 is a block diagram explaining an outline of correction to influence of beam hardening or other factors, the correction being performed by a data processing apparatus.

In the foregoing basic configuration, as shown in FIG. 4, the data processing apparatus 12 acts as one of key parts of the processor 35. The data processing apparatus 12 is provided with, in terms of a software scheme or a hardware scheme, at least, an information acquisition unit 51 (serving as information acquiring means) and a pixel data calculation unit 52 (serving as pixel data calculating means). The information acquisition unit 51 acquires, based on the detection signal from the detector, information showing a thickness t of the object and an average linear attenuation coefficient $\mu$ in a transmission direction of fluxes of the X-rays, in each of the energy bins. The pixel data calculation unit 52 calculates, based on the information from the information acquisition unit 51, pixel data composed of pixel values each obtained by multiplying addition information by the thickness t, the addition information being obtained by mutual addition of the average linear attenuation coefficients $\mu$ in the respective energy bins. Hence, a relative decrease caused due to the beam hardening in an amount of X-rays transmission through the object in the lower energy ranges is prevented from being influenced largely. This results in suppression of noise in generated X-ray images of an object and a higher contrast of the images. In parallel, it is possible to secure a quantitative analysis of the object on the basis of thicknesses t along the X-ray pass directions through the object.

By the way, both the information accusation unit 51 and the pixel data calculation unit 52 are allowed to perform their calculation schemes to each of the X-ray energy bins (or, to "each of the X-ray energy bins and each of the pixels P (or each of the pixel areas)"). Such calculation schemes can be performed with detection signals outputted from a signal-pixel X-ray detector or a single-pixel X-ray sensor. Moreover, such calculation schemes can be applied to detection signals from an X-ray spectrometer (for example, EMF123 type X-ray spectrometer, made by EMF Japan Co., Ltd.).

In addition, the data processing apparatus 12 can also be provided with an image data generation unit (serving as image data generating means) 53 and an image data storing and presenting unit (serving as image data storing/presenting means) 54. Of these, the image data generation unit 53 generates, as image data whose pixel values are the pixel data, data of an average absorption value image. the image date storing and presenting unit 5 stores or presents the image data. By these units, the data of the average absorption value image can be stored and/or displayed as images.

<Correction of Counts>

In the present embodiment, it is assumed that there is provided a system in which X-rays having a continuous energy spectrum are radiated to an object, and the X-rays which has been transmitted through the object are discriminated into, for example, a plurality of energy bins, $Bin_1$ (i=1, 2, ...) in order to accomplish photon counting detection for the counts.

In this system, the characteristics of μt, which are calculated as a ratio between input and output photon counts in each X-ray energy bin, BIN ($\mu t = -\ln$(output count $Cl_i$/input count $Co_i$: i=1, 2, ...)), are shifted from the linear line (i.e., target characteristics) each passing the origin of the foregoing coordinate system, depending on thicknesses t of substances of an object in the X-ray transmitted direction, thus providing characteristics different from those obtained when the object is subjected to radiation of monochromatic X-rays. The reasons for this shift include the beam hardening and the heeling effect in each of the X-ray energy bins, BIN, and charge shearing occurring at pixels of the semiconductor detector, so that the present inventors have paid attention this shift. Measured X-ray attenuation amounts μt are corrected with use of multiplication coefficients such that shifted curves of the X-ray attenuation amounts μt agree with linear lines passing through the origin and having gradients=linear attenuation coefficients $\mu_{io}$ (i.e., constant values: not functions of the thickness t). These linear characteristics presenting such gradients $\mu_{io}$ become target characteristics corresponding to monochromatic X-rays. By way of example, the target characteristic is set in each X-ray energy bin, BIN, and at each pixel of the detector.

The foregoing multiplication coefficients are data serving as the correcting data, and obtained previously using a calibration (correcting) phantom having a plurality of materials of which components are known and of which thicknesses are also known.

This phantom is made of the same substances as those composing an object or of substances composed of materials which can be regarded as being similar to the object in terms of an effective atomic number. The effective atomic number is defined as an average atomic number Zeff of an object when the object is made of a plurality of substances (materials) (for example, refer to Isotope News, issued August 2014, No. 724, "New X-ray imaging for visualizing the effective atomic number Zeff"). Additionally, "the same substances as an object" is defined as substances whose materials have the same composition (the same kind of materials). Moreover, according to a knowledge of the inventors, "the substances composed of materials which can be regarded as being similar to the object in terms of an effective atomic number" can be defined as materials having an effective atomic number falling into a range of ±5 of the effective atomic number of an object, for example. In particular, when it is desired to obtain, with accuracy, types and/or properties of substances (such as foreign matters) which may be contained in an object in actual imaging (for example, when it is desired to have, with precision, a mammary gland content rate in mammography), a knowledge has been obtained such that it is desired to have a phantom whose materials have an effective atomic number falling into a range of ±2 of the effective atomic number of an object". For example, if an object has an effective atomic number of 7.2, it is desired that the phantom is composed of materials whose effective atomic number is 7.2±5, more desirably, 7.2±2.

The background of these numerical ranges will now be described by referring to a beam hardening correction which is necessary for material identification in the mammography. If the breast has no lesions, states of the beast can be expressed by a ratio of the mammary glands and fat. Hence, it is good if the beam hardening correction can be performed by a phantom having the same materials as tissues expressed by a 50% of mammary glands and a 50% of fat. However, it is actually diffident to obtain such a phantom, so that there is almost no option but to produce a phantom by combining ordinary generally-known materials. This time, for trying to conduct the beam hardening correction, the inventors made a phantom equivalent to a 50% of mammary glands and a 50% of fat, from breast-equivalent plate phantoms of XUR types made by KYOTO KAGAKU Co., LTD. The correction results were good. Meanwhile the inventors tried to make a aluminum phantom to conduct beam hardening correction for the breast, but it was difficult to obtain material identification with higher precision, because of dependency of the correction on tissue thicknesses. These experiments show that it is important to produce correcting data (i.e., calibration data) by using a phantom whose materials are similar to those of an object, which materials should be selected with consideration of the effective atomic number and to conduct the beam hardening correction using such correcting data.

First, as one example of previous measurement which uses the foregoing phantom, a relationship between respective X-ray energy bins and X-ray attenuation amounts will be explained in a case where the number of X-ray energy bins is three.

Figure 5:
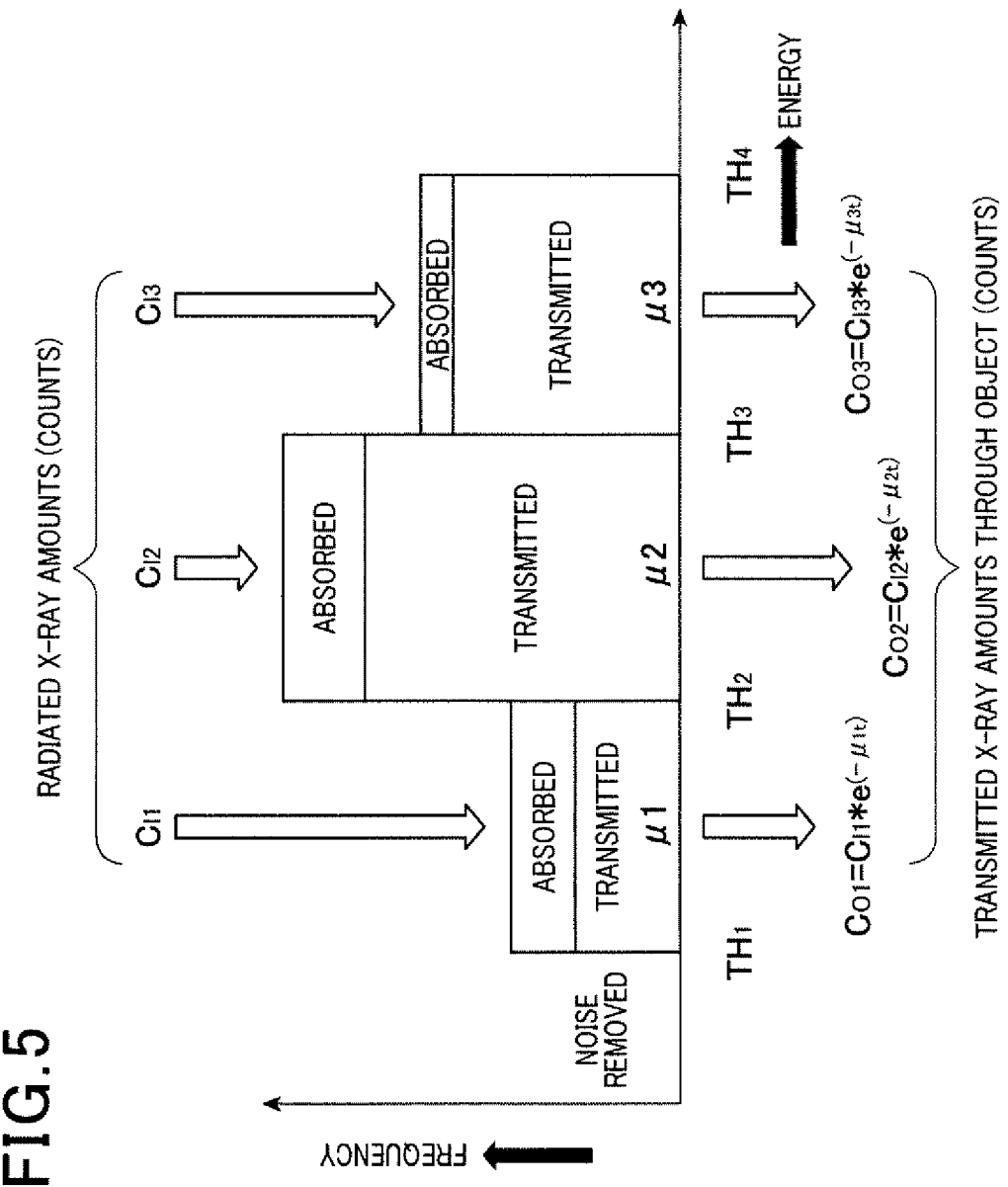
FIG. 5 is a graph explaining a relationship between incident amounts (counts) of the X-ray photons and transmitted amounts (counts: measured values) thereof in the respective X-ray energy bins.

As shown in FIG. 5, the X-ray energy bins, $Bin_1$ to $Bin_3$, shown in FIG. 3 are pictorially assigned to the lateral axis in FIG. 5 and measured values of X-ray photons counted in each of the X-ray energy bins, $Bin_i$ (i=1 to 3) is assigned, as counts, to the longitudinal axis. When an X-ray beam having a continuous energy spectrum is radiated, X-ray photons are absorbed and transmitted in and through an object in each of the X-ray energy bins, Bini, and the transmitted X-ray photons are detected. Assuming that the numbers of incident X-ray photons in the respective X-ray energy bins, $Bin_i$ are $Cl_1$, $Cl_2$, $Cl_3$ and the number of transmitted (emitted) X-ray photons are $Co_1$, $Co_2$, $Co_3$, the following expressions can be provided, $$Co_1 = Cl_1 \cdot e^{(-\mu 1 t)} \quad (1)$$

$$Co_2 = Cl_2 \cdot e^{(-\mu 2 t)} \quad (2)$$

$$Co_3 = Cl_3 \cdot e^{(-\mu 3 t)} \quad (3)$$

wherein $\mu_1$, $\mu_2$, and $\mu_3$ can be referred to as imaginary average linear attenuation coefficients in the respective X-ray energy bins, Bin; (in other words, linear attenuation coefficients provided to an effective energy amount in the respective energy bins). Meanwhile, the factor "t" is a depth (thickness) of the path in the X-ray transmission direction passing through the object. This case is premised on a condition that the imaginary average linear attenuation coefficients $\mu_1$, $\mu_2$, and $\mu_3$ in the respective X-ray energy bins, $Bin_1$, are not dependent on the thickness t.

FIG. 6 shows actually measured results of the thicknesses t and attenuation values $\mu_i t$ (i=1 to 3) of aluminum (Al) adopted as a substance, under radiation of X-rays with a continuous-energy spectrum. In parts (A), (B) and (C) of FIG. 6, there are shown characteristics of the imaginary attenuation values $\mu_i t$ in the order of the lowest energy bin, $Bin_1$, an intermediate energy bin, $Bin_2$, and the highest energy bin, $Bin_3$. In these graphs, the linear characteristics show calculated values (i.e., theoretical values) of imaginary attenuation amounts $\mu_i t$ obtained when monochromatic X-rays having a central X-ray energy in each of the X-ray energy bins, $Bin_i$, are radiated. In contrast, when X-rays having a continuous energy spectrum are radiated, characteristics showing the imaginary attenuation amounts $\mu_i t$ are shifted from the linear characteristics, and degrees of their curves become larger in lower X-ray energy bins compared with higher X-ray energy bins. These curved characteristics can be approximated by quadratic curves. These curves show that the measured values are influenced by various factors, such as beam hardening which is a main factor, and the degree of such influence increases as an increase in the thickness t.

When the characteristics showing the attenuation amounts $\mu_i t$ shift from linear characteristics (corresponding to those obtained in radiation of monochromatic X-rays) passing the coordinate origin, scatter points also deviate from a certain range of distribution centering one point in a three-dimensional scatter diagram, which is provided from an object made of the same substances having different thicknesses. In other words, this means that the assumption that linear attenuation coefficients $\mu_i$ to the effective energies in the respective X-ray energy bins do not depend on the thicknesses is not realized.

That is, this situation makes it difficult to estimate a distribution of scatter points or lower reliability of the estimation, which is required for substance identification (identifying, determining or estimating the type or property of a substance), which is a preferred example for the correction stated in the present embodiment.

<Acquisition of Correcting Data>

Hence, correcting data are previously set, which correct the shifted curves of the imaginary attenuation values so as to agree with the linear line (i.e., the linear target characteristic), which corresponds to that obtained in the radiation of designated monochromatic X-rays each of the X-ray energy bins. For example, the correcting data are set to be multiplication coefficients to correct the foregoing curves to linear lines each passing the coordinate origin.

Figure 7:
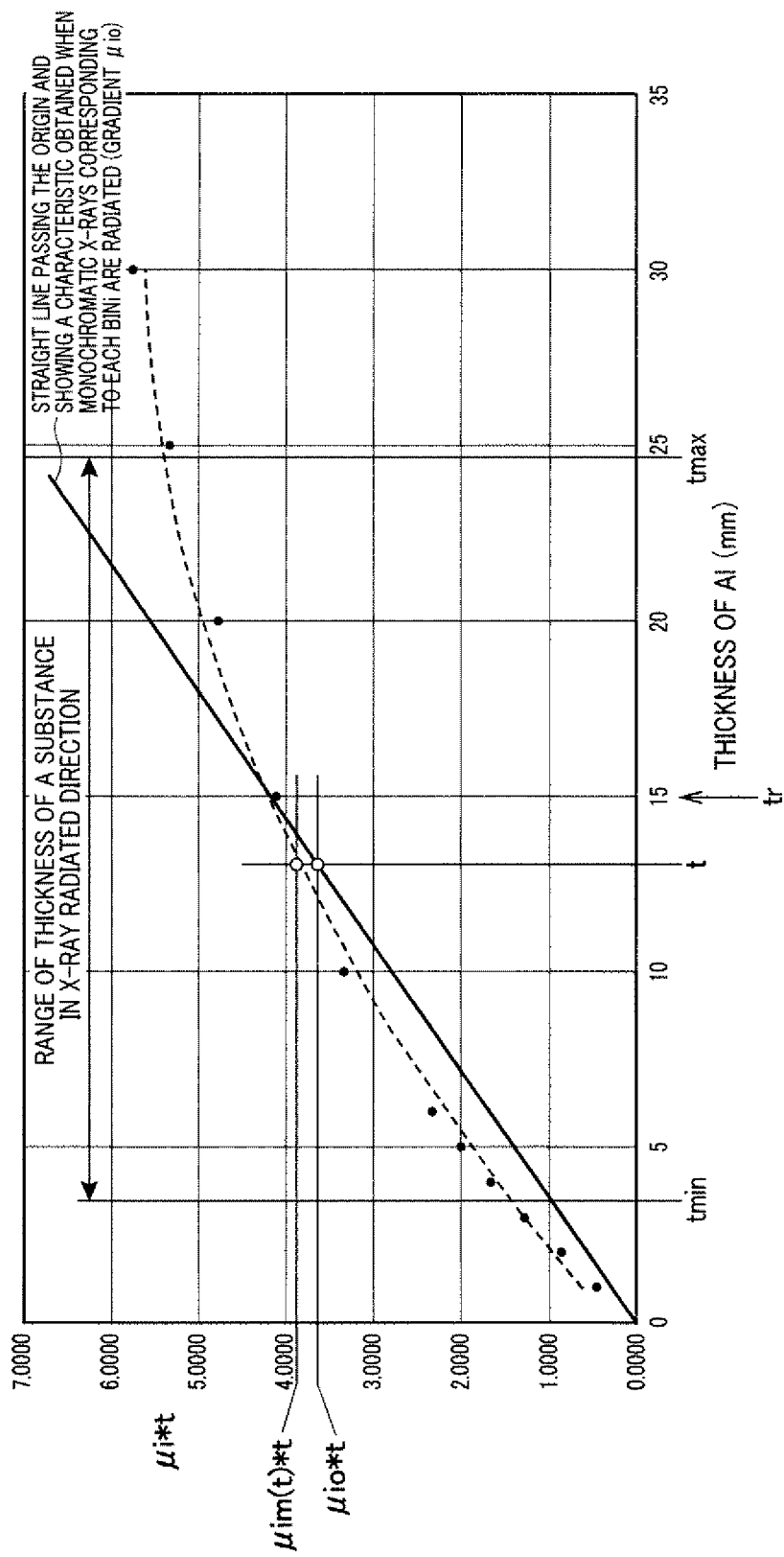
FIG. 7 is a graph explaining how to generate correcting data for correcting influence of the beam hardening and other factors.

Referring to FIG. 7, how to prepare for the correcting data in advance will now be described. The correcting data are acquired before an actual X-ray examination or X-ray imaging, and stored in the ROM 33, that is, storage means. When an examination or imaging is actually carried out, the correcting data are read from the ROM 33, and used to correct, at respective pixels P or pixel areas PA, measured values acquired in the form of frame data.

In FIG. 7, the longitudinal and lateral axes are given the same dimensions as those explained in FIG. 6(A) to (C) and are representative of such axes shown in FIG. 6(A) to (C). In this example, it is assumed that the substance is made of aluminum (Al). FIG. 7 exemplifies characteristics, in which a curve shows imaginary attenuation values measured at thicknesses t of the substance in the X-ray transmitted (projected) direction and a linear line shows imaginary attenuation values $\mu_i t$ (i=1 to 3) at the thicknesses t in the X-ray transmitted direction.

Of these characteristics, the linear line shows a characteristic of the imaginary attenuation values $\mu_i t$ obtained when monochromatic X-rays having an effective energy value in each of the X-ray energy bins, $BIN_i$ (1=1 to 3). This linear line passes through the origin of this two-dimensional coordinate at a gradient $\mu_{i0}$, and can be obtained by approximate calculation applied to a curved line detailed later.

Meanwhile, the curved line exemplifies a characteristic obtained with the thicknesses t in the X-ray transmitted direction, when X-rays having a continuous energy spectrum (i.e., the polychromatic X-rays) are radiated to a substance made of aluminum. Since the polychromatic X-rays are used, the characteristic is curved, not along a straight line, due to the foregoing beam hardening or other physical factors. The characteristic shown by imaginary attenuation values $\mu_i t$ for the polychromatic X-rays can be obtained, for example, by using a phantom having different portions whose thicknesses t are known and different from each other.

If it is assumed such that:

$\mu_i m(t) \cdot t$: an attenuation value calculated at a thickness t and in each of X-ray energy bins, $BIN_i$ ($\mu_i m$ indicates an imaginary linear attenuation coefficient and t indicates a thickness along an X-ray path passing through the object), $\mu_i t$: a linear attenuation coefficient $\mu_{io}$ (not a function of t) corresponding to monochromatic X-rays at a thickness t in each of X-ray energy bins, BIN, and Ci(t): multiplication-correcting coefficients for replacing the linear attenuation coefficients $\mu_{io}$ with those which do not depend on the thickness t, the multiplication-correcting coefficients $C_i(t)$ can be calculated based on:

$$\mu_{io} \cdot t = C_i(t) \cdot \mu_i m(t) \tag{4}$$

Hence, the multiplication-correcting coefficients $C_i(t)$ are provided as correcting data.

Specifically, function forms which are candidates for one or more correction coefficients $C_i(t)$ are estimated, and any function form (for example, the quadratic function) is used for approximation of the curved characteristics. The correcting data $C_i(t)$ are then obtained from the characteristics of the X-ray attenuation amounts $\mu_i m(t) \cdot t$ acquired at one or more thicknesses t, as a value which minimizes a value calculated based on the following formula:

[Number 1]

$$\sum_{tmin}^{tmax} [(C_i(t) \cdot \mu_{im}(t) - \mu_{i0})^2 t^2 \tag{5}$$

(i=1, 2, 3)

This formula (5) involves tmin and tmax, which regulates a wide range which includes a lower value and an upper value of thicknesses of an object in the X-ray flux transmitted direction. The tmin and tmax can be set imaginarily when the object is examined.

The foregoing formula (5) includes a multiplication term, which often results in generating a larger error rate to the correcting data $C_i(t)$ in a thinner range of the object thickness. It is therefore desired, as one counter measure, to provide a mode that the error rate to the correcting data $C_i(t)$ does not depend on the thickness t. For that reason, the foregoing formula (5) can be changed to the following formula (5') in which the correcting data $C_i(t)$ can be calculated as values which minimize a value of the formal (5').

[Number 2]

$$\Sigma_{tmin}^{tmax}[C_i(t)\mu_{im}(t)-\mu_{i0}]^2 \tag{5'}$$

(i=1, 2, 3)

The resultant correction data $C_i(t)$ calculated for the respective thicknesses t are stored in the first data storage area 33B of the ROM 33. Additionally, approximated data showing the foregoing function form (for example, the quadratic function) are also stored in the second data storage area 33C.

(Phantom)

Hence, in the present embodiment, various phantoms are used to previously measure (previous measurement) the imaginary attenuation values $\mu_i m(t) \cdot t$ shown in FIG. 7, at every pixel, so that the foregoing correcting data Ci(t) can be obtained at every pixel.

As phantoms, various phantoms are used, which are composed of known type of substances (such as a water phantom imitating a pepper or an aluminum phantom imitating aluminum).

Figure 8:
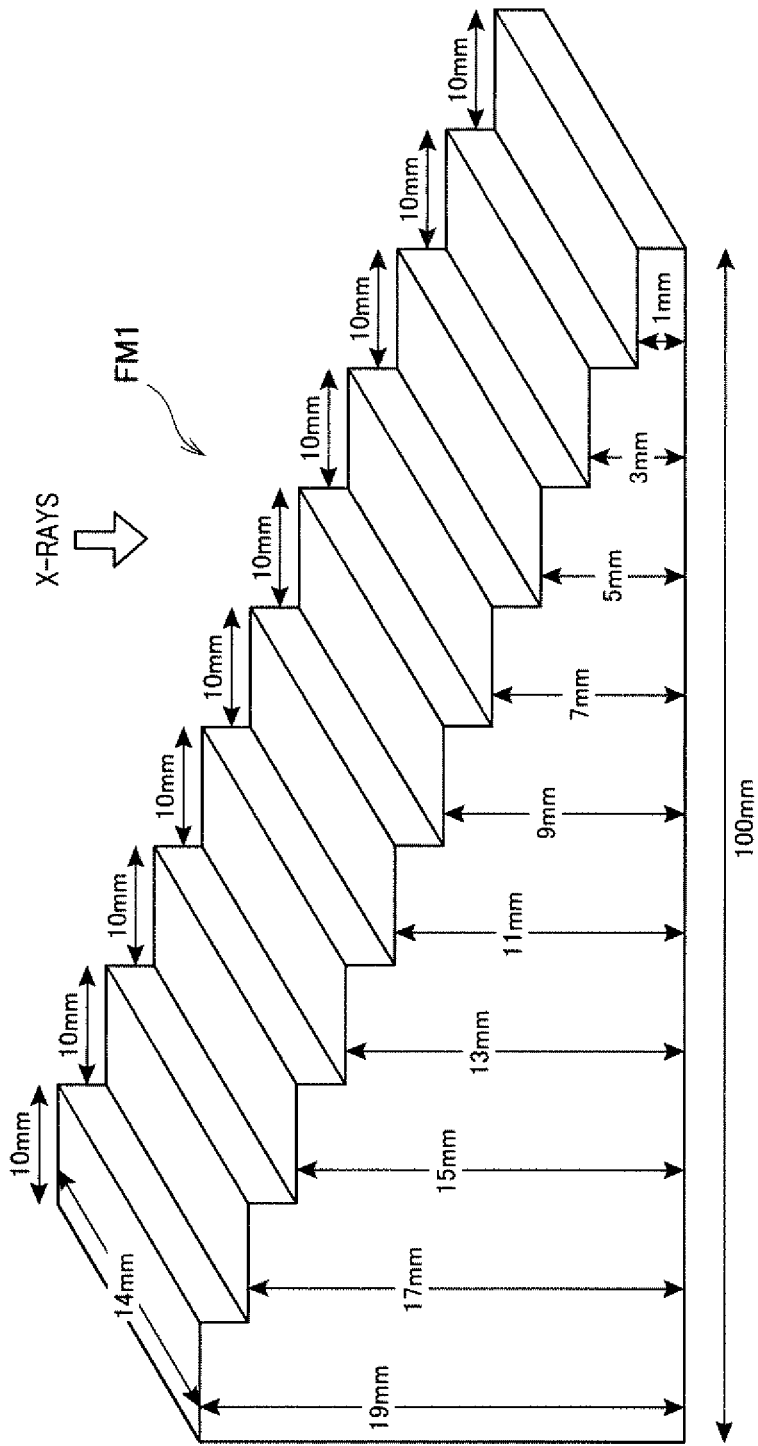
FIG. 8 is a perspective view exemplifying a phantom (calibration phantom) made of a known substance or a material imitating the known substance, the phantom being formed to have a plurality of steps having known thicknesses and being used for previously acquiring the correcting data.

FIG. 8 pictorially exemplifies a pepper phantom FM1, which can be used in an X-ray foreign matter inspection for inspecting whether peppers being inspected as food contain with foreign matters such as metals (such as aluminum). As a main component of the peppers is water, the phantom FM is provided as a container with water filled in, in which the container is a higher X-ray transmission rate. This phantom is structured to have portions whose heights correspond to thicknesses t (t=1 mm to 19 mm) changing stepwise in the X-ray transmission direction. This range of the thicknesses t is decided to cover possible material thicknesses of the peppers during the foreign matter inspection. Further, as to a phantom imitating foreign matter which may be contained in objects such as food items, it is ordinary that the foreign matter is smaller than the objects. As a result, in the case of the aluminum phantom, it is sufficient that the two or more stepwise portions have known thicknesses slightly changed step by step and the minimum and maximum thicknesses are also smaller.

Figure 9:
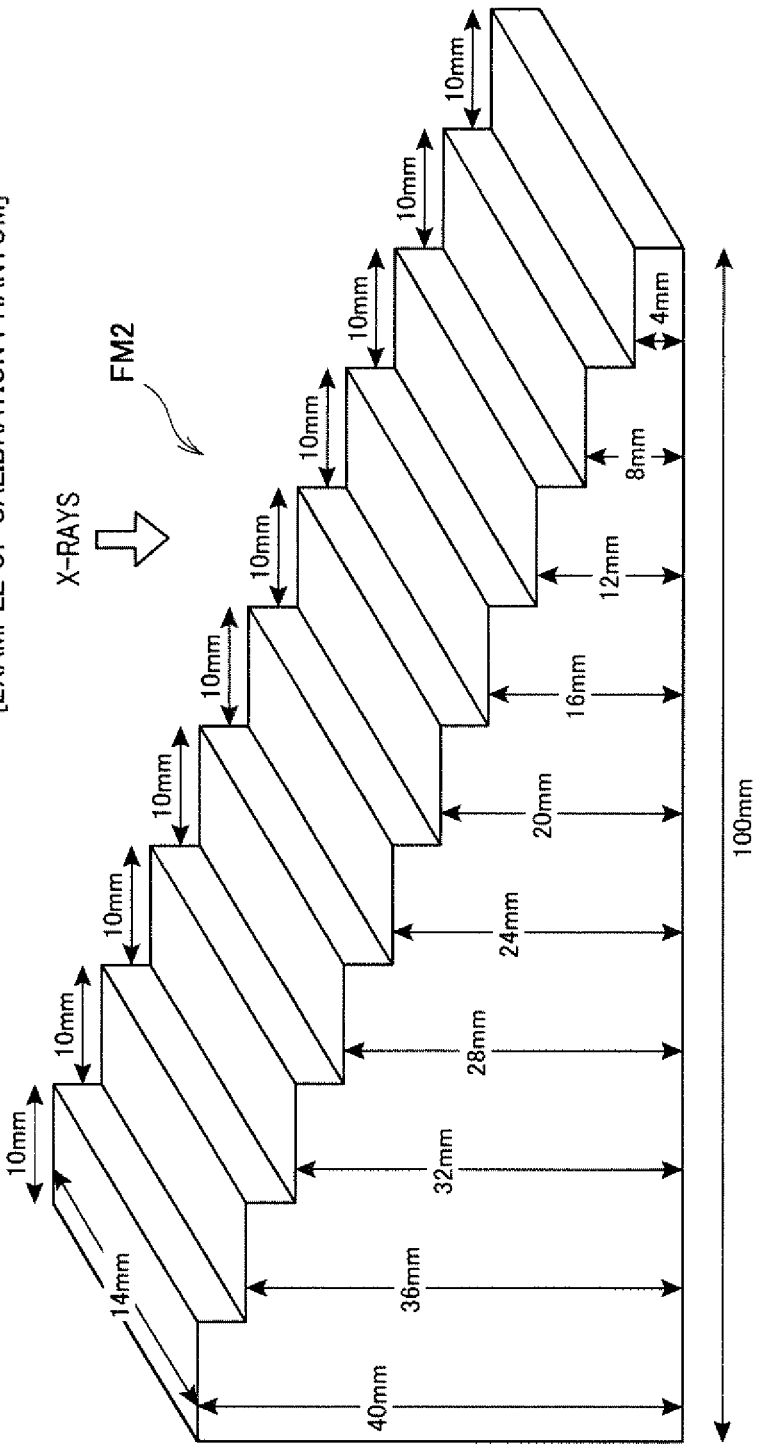
FIG. 9 is a perspective view exemplifying another phantom (calibration phantom) made of a known substance or a material imitating the known substance, the phantom being formed to have a plurality of steps having known thicknesses and being used for previously acquiring the correcting data.

FIG. 9 exemplifies another phantom FM2, which has a mixture of human muscle and adipose 70%. This phantom FM2 has different portions whose heights are set to cover actually supposed inspection thicknesses, so that, by way of example, there is stepwise structure whose heights change from 4 to 40 mm, at every 4 mm step.

(Example of Whole Processing)

Figure 10:
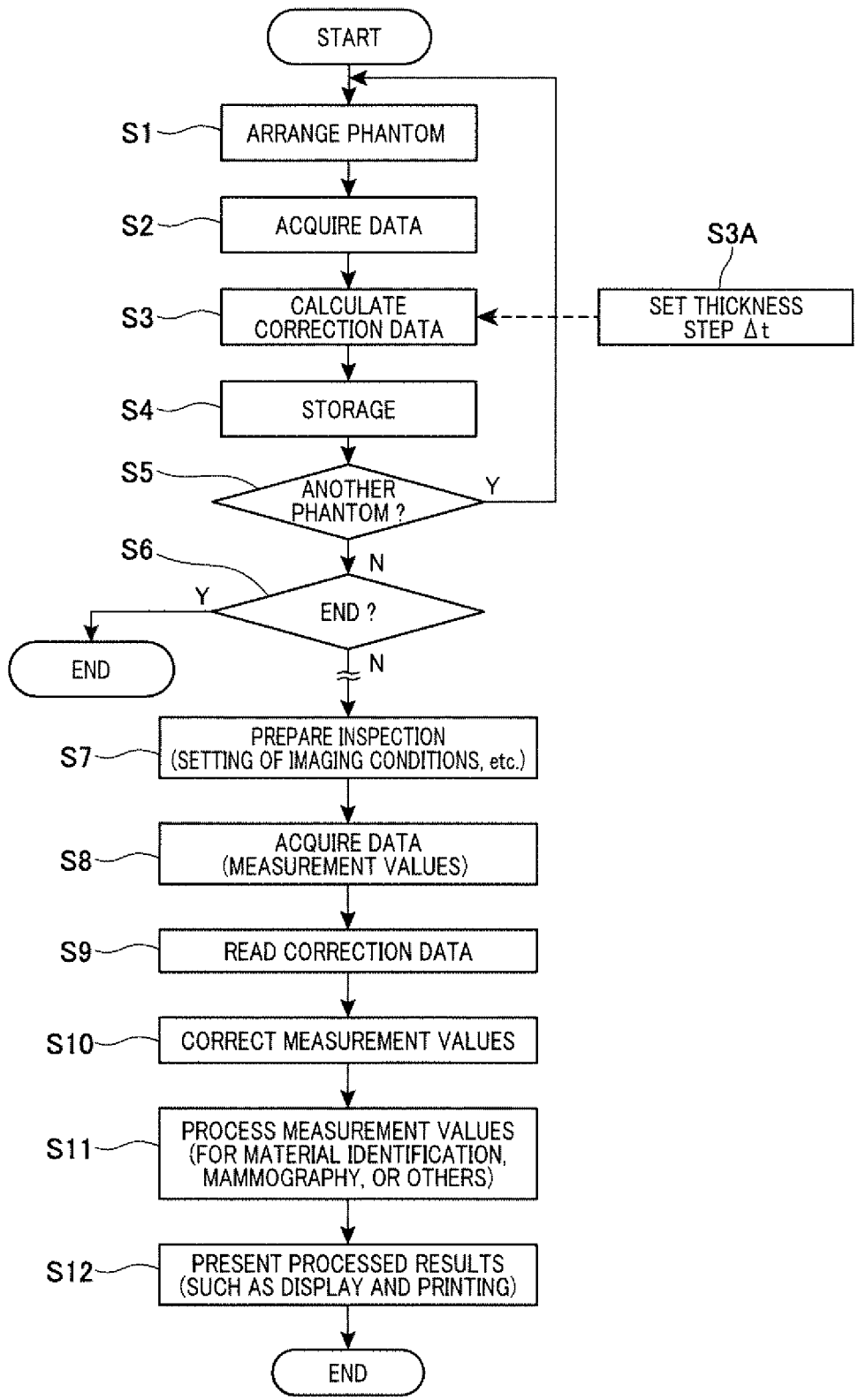
FIG. 10 is a flowchart exemplifying an outline of processes from acquisition of correcting data, and correction and usage of measured data (the flowchart also explaining a first variation)

The processor 35 of the data processing apparatus 12 performs a process exemplified in FIG. 10. The processor 35 instructs an operator to arrange a desired substance phantom FM1 (FM2) at a determined inspection position in the X-ray device 10 (step S1). After this arrangement, the X-ray device 10 is driven to scan the phantom FM1 with X-rays in order to acquire counted values for the phantom (step S2). The processor 35 then calculates correcting data $C_i(t)$ (step S3), and store in the first data storage area 33B of the ROM 33 for preservation (step S4). To calculate such correcting data $C_i(t)$, the foregoing formula (5) or (5') can be used.

Then the processor 35 confirms whether or not another phantom is to be subjected to the similar calculation, interactively with the operator (step S5). If another phantom is desired for generating the correcting data, the processing returns to step S1 to repeat the foregoing process with the next phantom FM2 (FM1). The number of phantoms is not limited to two, but many other phantoms are usable depending on types or properties of objects being inspected or foreign matter. For each phantom, the correcting data are prepared.

When this series of the previous measurement and correcting data calculation for the phantoms are desired to end, the processing is also ended (step S6, YES). In contrast, the processing will not be ended (step S6, NO), the process for the inspection is performed at and after step S7.

First, the processor 35 performs, interactively with the operator, preparation work for the inspection, which includes selection of an object being examined and setting of imaging conditions (step S7). Then the processor 35 drives the X-ray device 10 to an X-ray scan (for example, a foreign matter inspection: step S8). By this scan, frame data of the object, i.e., measured values are acquired, for example, at the respective pixels P in each of the X-ray energy bins, $Bin_1$ (for example, i=1, 2, 3).

The processor 35 then reads the correcting data $C_i(t)$ of the object (for example, a food item (e.g., peppers)), which have been stored in the first data storage area 33B of the ROM 33 (step S9). The processor 35 calculates linear attenuation values $\mu_i o^* t$ corresponding to the monochromatic X-rays, by multiplying, by the correcting data $C_i(t)$, the imaginary attenuation values $\mu_i o^* t$ obtained from the measured values (step S10). This results in correcting the imaginary attenuation values $\mu_i m(t)^* t$, which are along a curved characteristic without being along a linear characteristic. This can be regarded as a comprehensive calibration which was performed after the actual measurement, as if error factors, which cannot be understood without actual X-ray detection, have been understood even before the actual X-ray detection. This correction (i.e., calibration) can be performed at every pixel area PA.

After this, the processor 35 process the measured values interactively with the operator to check whether or not foreign matter which may be contained in the object, identify the type of foreign matter, and/or carry out other necessary processes (step S11). When identifying foreign matter, the correcting data CA) generated by using phantoms made of aluminum and/or other substances are used in the same manner as described.

This identification technique is known, for example, by patent publications of JP-A 2013-119000 and WO 2014 181889(A1). The present inventors have proposed improvements of such identification technique by patent publications of JP application numbers 2015-023446 and 2015-85551.

Further, the processor 35 presents processed results of the measured values via, for example, various display and printing modes (step S12), before ending the process.

As examples of presentation of the processed results, exemplified are presenting a three-dimensional scatter diagram, an absorption vector length image and/or an average absorption value image. These scatter diagram and images can be displayed and/or presented selectively or together.

<Concerning Three-Dimensional Scatter Diagram>

Figure 11:
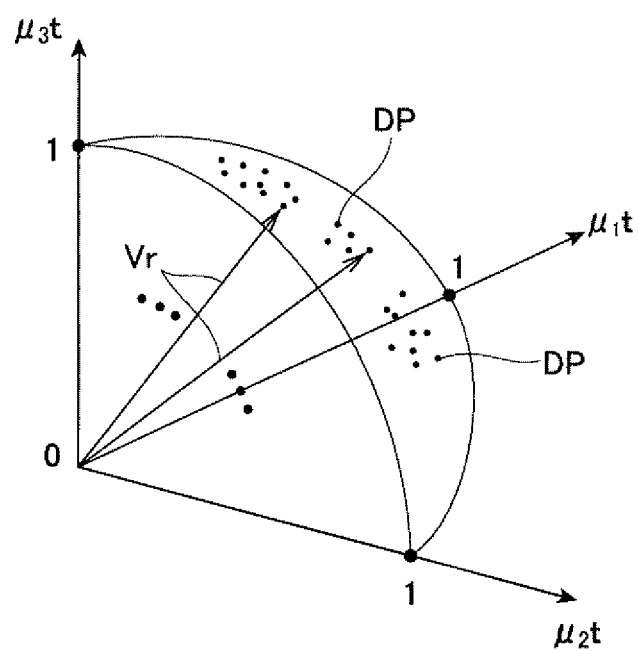
FIG. 11 is an illustration pictorially explaining a concept of a three-dimensional scatter diagram.
Figure 12:
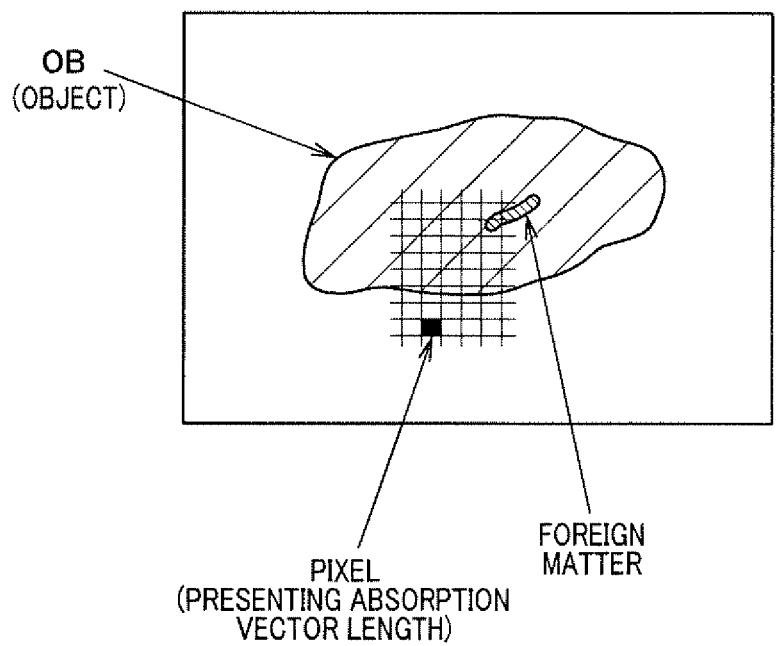
FIG. 12 is an illustration pictorially explaining a concept of an absorption vector length image.
Figure 13:
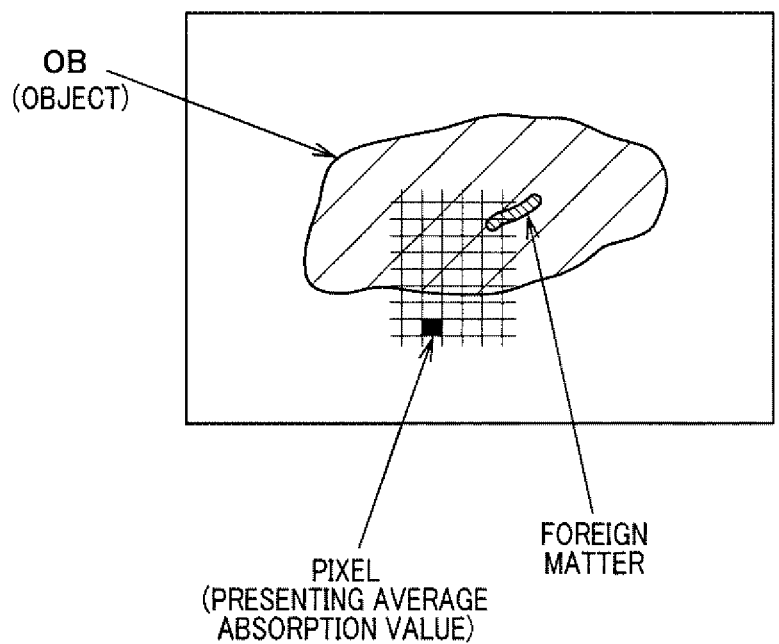
FIG. 13 is an illustration pictorially explaining a concept of an average absorption value image.

In the present embodiment, the linear attenuation amounts $\mu_i t$ have three degrees of freedom, because of use of three X-ray energy bins, $Bin_i$ (i=1, 2, 3). Hence, a three-dimensional vector ($\mu_1 t, \mu_2 t, \mu_3 t$) can be set at each pixel, and from this, a three-dimensional linear attenuation vector ($\mu_1, \mu_2, \mu_3$) can be obtained. A length of this vector $\mu_1, \mu_2, \mu_3$), that is, a linear attenuation vector length, $(\mu_1^2+\mu_2^2+\mu_3^2)^{1/2}$ can be used as a denominator in calculating a normalized three-dimensional vector (herein referred to as a linear attenuation vector) from a formula of:

$$(\mu_1, \mu_2, \mu_3)/(\mu_1^2 + \mu_2^2 + \mu_3^2)^{1/2} \quad (6)$$

where the factor of the thickness t disappears from this linear attenuation vector. When a three-dimensional Cartesian coordinate system whose three axes are $\mu_1 t$, $\mu_2 t$, and $\mu_3 t$ is set, the three-dimensional linear attenuation vector has a start point at the origin of the three-dimensional coordinate system and an end point on a spherical surface, of which radius is 1. This three-dimensional linear attenuation vector is calculated as each pixel and mapped in the three-dimensional coordinate system, resulting in that the end points are mapped within a certain area around a point mapped on the spherical surface. This area is composed of an aggregation of scattered points mapped with statistical errors. The inventors refer to this three-dimensional scatter-point map as a three-dimensional scatter diagram, which is exemplified in FIG. 11. In FIG. 11, a reference symbol Vr indicates a three-dimensional linear attenuation vector and a reference symbol DP indicates scattered points.

How the end points (scatter points) of the linear attenuation vectors are mapped on the spherical surface, that is, in the three-dimensional scatter diagram, is inherent to the type itself of a substance contained in an object. In other words, the substance type is changed, the scatter points are also changed, which is true from a theoretical viewpoint. These changes are led to identification of types of substances (materials). This was confirmed by a simulation carried out by the inventors.

<Concerning Absorption Vector Length Image>

Moreover, the vector length at each pixel can be calculated by a formula of $t(\mu_1^2 + \mu_2^2 + \mu_3^2)^{1/2}$.

The inventers refer to this scalar value as an absorption vector length (or a pseudo-absorption value). This absorption vector length can be formed as a two-dimensional image whose pixels are indicated by the absorption vector length. The inventers refer this two-dimensional image as an absorption vector length image (or a pseudo-absorption image), which is pictorially exemplified in FIG. 12.

<Concerning Average Absorption Value Image>

Furthermore, when imaginary average linear attenuation coefficients in the three energy bins, $Bin_1$ to $Bin_3$, which are liner attenuation coefficients to effective energy amounts in the respective energy ranges, are expressed by $\mu_1$, $\mu_2$, $\mu_3$ and an object has a thickness t in an X-ray transmission direction, the pixel value at each of the pixels can be provided based on the following formula:

$$\text{pixel value} = t \cdot (\mu_1 + \mu_2 + \mu_3)/3 \quad (8)$$

or $$\text{pixel value} = t \cdot (a_1 \cdot \mu_1 + a_2 \cdot \mu_2 + a_3 \cdot \mu_3)/3 \quad (9)$$

where $a_1$, $a_2$, $a_3$: weighting coefficients which are 0 or more positive real numbers, and which meet $a_1 + a_2 + a_3 = 3$.

That is, the pixel values can be obtained as scaler quantities depending on the thicknesses t. The foregoing formulas have a denominator of 3. The reason for this is to calculate an averaged value over the three energy bins, Bin1 to Bin3, that is, all the energy bins.

In the foregoing formula, the weighting coefficients $a_1$, $a_2$, and $a_3$ can be set as default values or can be changed by an operator during operator's work such as interpretation. The condition for the coefficients, "$a_1 + a_2 + a_3 = 3$," is intended to perform weighted average, so that if a pixel value is treated by multiplying the weighted average value by a real number, this condition can be removed.

An image composed of pixels whose pixel values are calculated as stated is defined as an average absorption value image by the present inventors. An example of this average absorption value image is pictorially shown in FIG. 13, in which each of the pixel has a pixel value calculated based on the forgoing formula (8) or (9). As a variation, the pixel value of each pixel may be given as a value calculated from pixel values of definite-number combined pixels surrounding each designated pixel.

The average absorption value image according to the present invention is not always limited to the application in which the three X-ray energy bins are defined in the continuous X-ray spectrum. For example, the number of X-ray energy ranges (bins) may be two depending on whether the energy is small or large. In such a case, the continuous X-ray spectrum can be divided into two energy ranges consisting of lower and higher energy ranges. To use such two energy bins, the information acquiring unit 51 shown in FIG. 5 is configured to acquire liner attenuation coefficients $\mu_1$ and $\mu_2$ in the lower and higher energy ranges respectively. Then the pixel data calculating unit 52 calculates average pixel values based on:

$$\text{pixel value} = t \cdot (\mu_1 + \mu_2)/2 \quad (8')$$

or $$\text{pixel value} = t \cdot (a_1 \cdot \mu_1 + a_2 \cdot \mu_2)/2 \quad (9')$$

where $a_1$, $a_2$: weighting coefficients which are 0 or more positive real numbers, and which meet $a_1 + a_2 = 2$.

In addition, the average absorption value image according to the present invention can be produced in a case where four X-ray energy bins (in a generalized form, n is a four or more positive integer) are section in the continuous X-ray spectrum. In this case, when it is assumed that liner attenuation coefficients $\mu_1, \ldots, \mu_n$ are given from the respective energy ranges, an average pixel value for each X-ray range is calculated based on:

$$\text{pixel value} = t \cdot (\mu_1 + \ldots + \mu_n)/n \quad (8'')$$

or $$\text{pixel value} = t \cdot (a_1 \cdot \mu_1 + \ldots + a_n \cdot \mu_n)/n \quad (9'')$$

where $a_1, \ldots, a_n$: weighting coefficients which are 0 or more positive real numbers, and which meet $a_1 +, \ldots, + a_n = n$.

<Example of Image Display Process>

Figure 14:
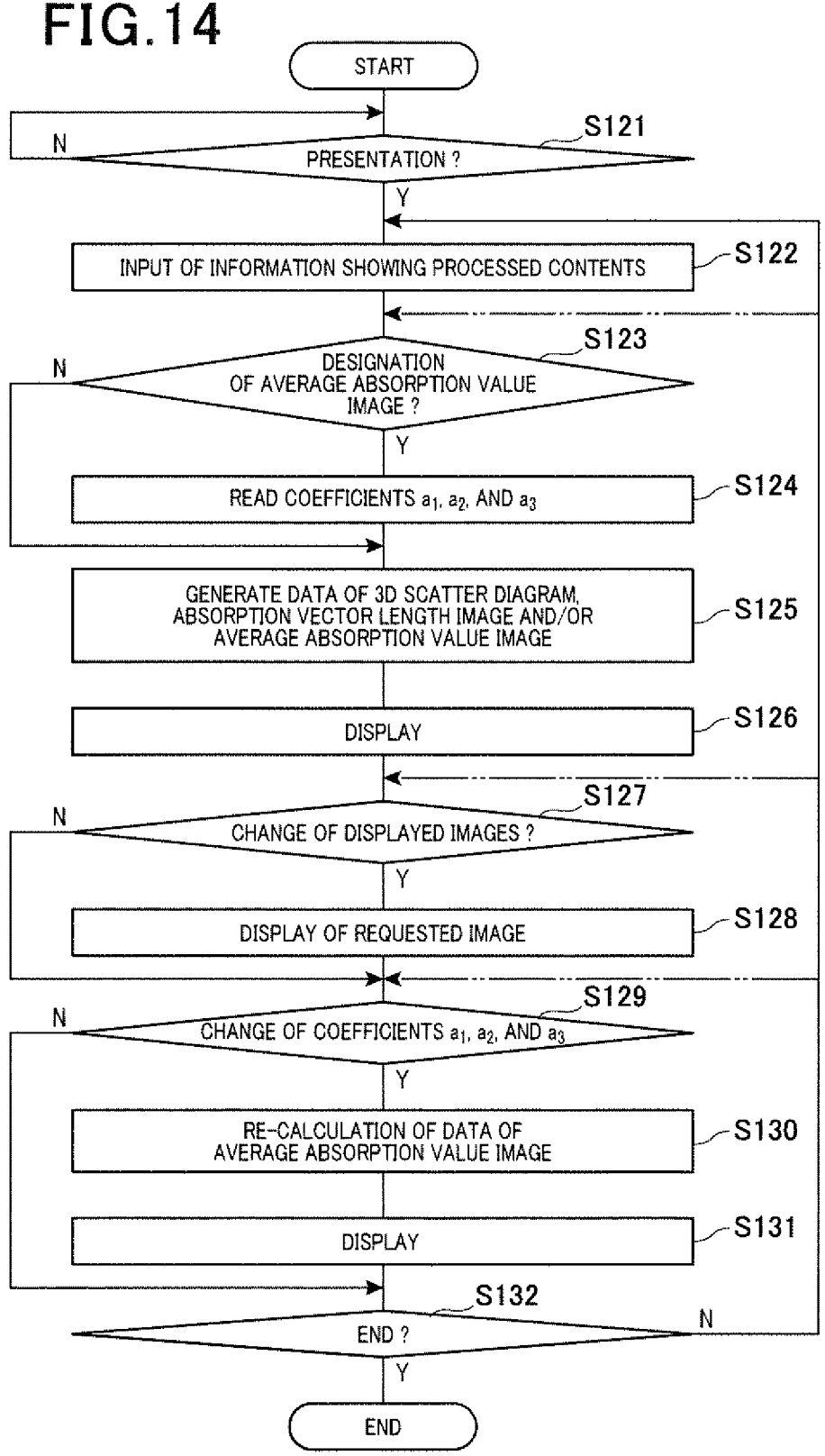
FIG. 14 is a flowchart explain a process according to an image display.
Figure 15:
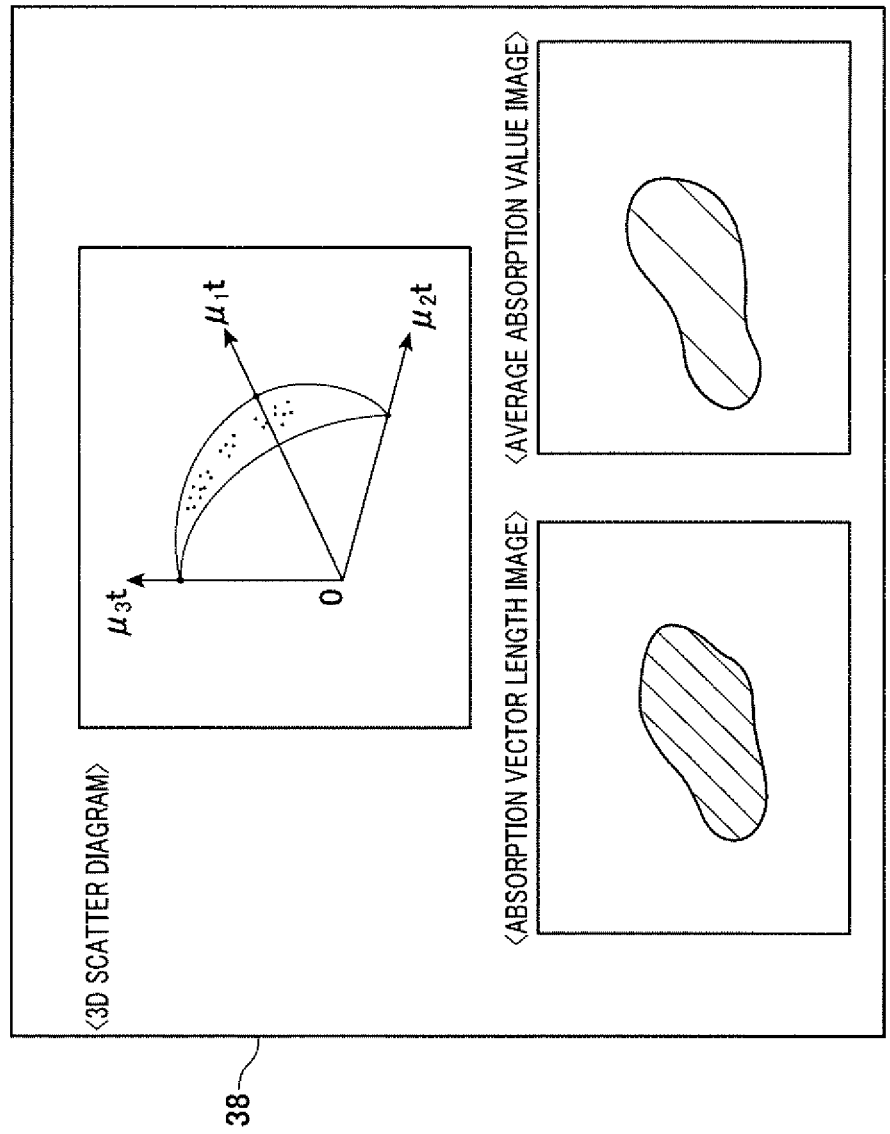
FIG. 15 is an illustration exemplifying image display on a display unit.

How the presentation step presenting results processed at step S12 will now be exemplified with reference to FIGS. 14 and 15. A program shown in FIG. 14 is previously stored in the program storage area 33A of the ROM 22. Hence, in response to an instruction for the process of FIG. 14, the processor reads the program from the program storage area 33A into its work area and performs the process according to the sequential steps described in the process.

The processor 35 first determines whether or not a presentation process should be carried out interactively with the operator (FIG. 14, step S121). When it is determined that the presentation process is necessary (YES at step S121), the processor 35 then receives information indicating the presentation process interactively with the operator (step S122). This information includes information showing which images should be selected, for displaying thereof, from the foregoing three-dimensional scatter image, absorption vector length image, and average absorption value image. Thus it is then determined whether or not the information includes information designating display of the average absorption value image (step S123). When it is determined that the average absorption value image is designated (YES at step S123), the processor 35 then decides default values or designated values of the weighting coefficients $a_1$, $a_2$ and $a_3$ interactively with the user.

The processor 35 then uses the information read at step S122, and calculates image data of at least one of the three-dimensional scatter diagram, the absorption vector length image, and average absorption value image, based on the formulae (6), (7), and/or (8) (or (9)), and stores the calculated image data into the image memory 36 (step S125). The processor 35 then displays the calculated image data on the display unit 38, every image type (step S126).

One example of the foregoing display is pictorially shown in FIG. 15. In this example, the three types of images, which are the three-dimensional scatter diagram, the absorption vector length image, and average absorption value image, are displayed in a divided display manner.

Further, the processor 35 queries to the interpreter about whether it is needed to change images to be displayed (step S127), and if an image display change is requested, image data of the change-requested image is displayed (step S128). By way of this display change, from a display state where the three-dimensional scatter diagram and/or absorption vector length image which have been displayed, the average absorption value image is displayed solely or a combination of both this average absorption value image and another image is displayed.

Furthermore, the processor 35 queries to the interpreter about whether the interpreter desires to change the weighting coefficients $a_1$, $a_2$ and $a_3$ for the average absorption value image (step S129). When it is determined YES, that is, changes of the weighting coefficients $a_1$, $a_2$ and $a_3$ are instructed, changed weighting coefficients $a_1$, $a_2$ and $a_3$ are used to calculate image data of the average absorption value image again and stores the calculated image data to in the image memory 36 (step S130). As an example of this image change, the weighting factor $a_1$ in the lower X-ray energy bin, $Bin_1$, is changed to adjust the affection of the number of X-ray photons in the X-ray energy bin, $Bin_1$, to all the X-ray energy bins. An average absorption value image updated in this way is displayed on the display unit 38 (step S131).

The foregoing steps are repeated with returning to step S122, S123, S127 or S129 until a process end is instructed.

As stated, the three-dimensional scatter diagram, the absorption vector length image, and average absorption value image can be selected and displayed arbitrarily. In addition, the weighing coefficients $a_1$, $a_2$ and $a_3$ can be changed arbitrarily in order to correct the influence of the beam hardening every X-ray energy bin. It is thus possible to provide the average absorption value image whose pixel values have scalar quantities showing a quantitative performance to an object thickness t in the X-ray path direction and whose CNR and contrast are well balanced.

<Simulation>

Simulations conducted by the inventors showed that the foregoing correction (or calibration) of error factors, such as beam hardening, which influence an X-ray spectrum, raises a depiction performance of a substance depicted in the three-dimensional scatter diagram, and the absorption vector length image and the average absorption value image show proportions to thicknesses of a substance, in comparison with the conventional techniques.

In this way, according to the X-ray device of the present embodiment, the detector is used which is capable of counting X-ray photons in each of a plurality of X-ray energy bins. Using this detector, an object is scanned with X-rays having a continuous energy spectrum. Errors of measured values can be reduced greatly, even though the measured values may contain error factors such as X-ray attenuated factors including beam hardening and heeling effect and circuitry factors such as charge sharing. It is thus possible to correct the measured values (counts) as if the measured values have been calibrated before the processing, thus raising reliably. When performing an image reconstruction or an analysis based on such measured values, the processes are more stable, thus being more reliable. When identifying the types or properties of substances based on the measured values, the identification can be conducted with higher precision.

Moreover, conventionally, even if in one X-ray energy bin and for the same substance, an effective energy raises with an increase in the substance thickness due to the beam hardening. Because of this influence, it is difficult to obtain a characteristic obtained by assigning a representative of monochromatic X-rays to a single X-ray energy bin. However, in the present embodiment, this difficulty can be overcome as if designated monochromatic X-rays are radiated in each of the X-ray energy bins so that X-ray photons virtually behave on the radiated monochromatic X-rays, and measured values in each of the X-ray energy bins are corrected accordingly. It is thus possible to reduce error factors in the counts due to the beam hardening and others, and reduce distortions, noise and other factors in inspection images and analyzed maps, thereby providing inspected information with higher reliability.

Specifically, the image data are calculated whose pixel values are composed of multiplied values each provided by multiplying information of addition among the average liner attenuation coefficients $\mu$ in the respective X-ray energy ranges by corresponding one of the thicknesses t along the X-ray beam paths. Although the beam hardening will cause a decrease of X-ray amounts (i.e., the number of X-ray photons) in lower X-ray energy ranges so that noise components increase relatively, the degree of such relative increase can be suppressed thanks to the foregoing calculated image data, compared with a known method of calculating pixel values based on the square of each linear attenuation coefficient $\mu$. Meanwhile, the beam hardening will cause effective energy amounts in the lower X-ray energy ranges to increase relatively, the liner attenuation coefficients $\mu$ become smaller. However, the relative noise reduction contributes largely to a reconstructed image, resulting in that the image can have an improved CNR and good image contrast, not lowering in the image contrast.

Moreover, since the pixel values of the average absorption value image are obtained as values multiplied by the object thicknesses t, quantitative performance to the thicknesses t can be provided. This also make it possible that, in the X-ray inspection, the quantitative performance to object thicknesses t in the X-ray path directions can be secured, due to a reduced effect of the beam hardening to the X-ray attenuation, which results in a suppressed noise of the image and a good contrast still maintained.

Depending on a composition of substances of an object being inspected, it is not always necessary to prepare for a plurality of sets of correcting data, but it is sometimes sufficient if a set of correcting data is prepared using a material similar in X-ray transmission characteristics to the main substance of an object. In this case, it may be possible to use such correcting data to apply material identification to other components of the object, with precision. For instance, in the mammography, there can be seen a composition of mammary grand, fat, malignancy, calcification, and others, it is sufficient to prepare correcting data using a material whose effective atomic number is similar to that of average elements such as mammary gland which is normal tissue and fat, which makes it possible to realized highly accurate material identification.

In addition, this correction method can also be applied to a system detecting X-rays transmitted through an object by using an X-ray detector (or X-ray sensor) provided with a single pixel or an X-ray spectrometer. Even if in such a system, provided that information about the photon counts is acquired statistically fully and with precision, it is definitely possible to perform meaningful material identification.

From another point of view, it is possible to apply the configuration of the present invention to detection of the weight and/or thickness of substances. Namely, this results from the foregoing embodiment in which the correction is performed to be according to a linear line about both X-ray attenuation values and substance thicknesses in which the line passes through the origin of the coordinate system. Accordingly, if an object is composed of main substances whose kinds are the same and the linear attenuation coefficients of the substances are known, the weights and thicknesses of the restive substances can be calculated accurately. As to X-ray weight measurement of objects, such measurement has already been realized in some X-ray in-line inspection apparatuses used in the food foreign-matter inspection. However, this measurement has been realized in only inspections directed to a simple composition of materials, such as vegetables, which are absolutely limited in their application ranges (such as thickness or object types). The photon counting detector has a wider dynamic range, the range of applications to which higher-accurate weight measurement is applicable can be spread greatly, as long as X-ray radiation conditions are adjusted so as not to make it zero counts in each X-ray energy bin. In addition, it is supposed that, unlike the present invention, it is difficult to easily estimate the thickness of an object by using the conventional techniques.

[Modifications]

The foregoing embodiment has been explained about how to acquire the correcting data, but it is possible to still develop this technique in various modified modes.

(First Modification)

First of all, the linear target characteristic explained with FIG. 7 can be modified in various modes. The foregoing target characteristic is just one example. How to generate the target characteristic, which has been stated, is also just one example and can be designed in another way.

For instance, a linear line can be set as a target characteristic which connects, as shown in FIG. 7, the origin of the coordinate system and an intersection point where a representative thickness $t_r$ of an object and an X-ray attenuation amount $\mu t_r$ corresponding to the representative thickness $t_r$. Such a representative thickness $t_r$ can be set by referring to a plurality of mutually different thicknesses t of a substance which is similar in type or which can be approximated in X-ray transmission properties to an object being examined. This target characteristic can be calculated by the processor 35 or an external processing device in advance, and data of the target characteristic can be stored in the first data storage area 33B of the ROM 33. At step 9 shown in FIG. 10 described, the data of such target characteristic is read from the first data storage area 33B of the ROM 33, and can be used for calculating the correcting data.

[Second Modification]

A second medication also relates to another way of setting the target characteristic.

This setting technique is to set a linear line serving as a target characteristic, which has a designated gradient and which passes the origin of the coordinate system. The gradient is set to be a linear attenuation coefficient calculated based on a theoretical value for an effective or fixed energy in each of the X-ray energy bins.

Figure 16:
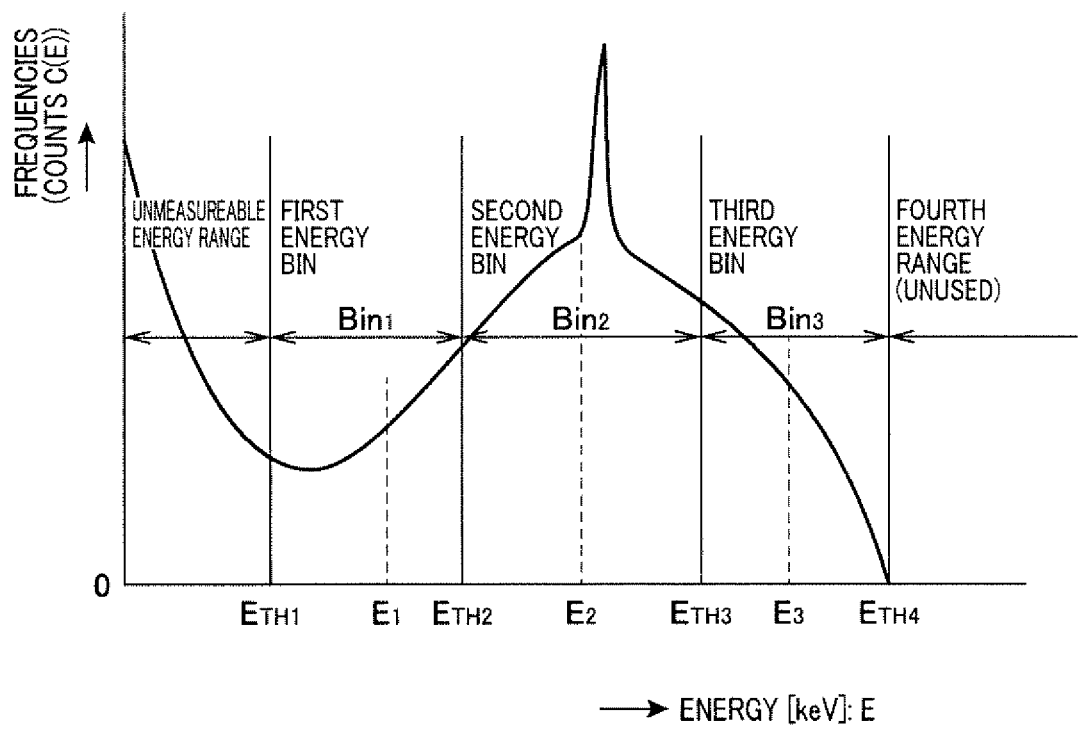
FIG. 16 is a graph showing an X-ray energy spectrum according a second modification.

A case which uses an effective energy in each of the X-ray energy bins will now be described. FIG. 16 pictorially exemplifies an X-ray energy spectrum. In this spectrum, similarly to that shown in FIG. 3, the three energy bins, $Bin_1$ to $Bin_3$, are set, in which an effective energy amount $E_i$ in the respective energy bins, $Bin_1$ to $Bin_3$, can be calculated based on the following formula:

[Number 3]

$$\int_{E_{THi}}^{E_i}(C(E)dE = \tfrac{1}{2}\int_{E_{THi}}^{E_{THi-1}} C(E)dE \tag{10}$$

wherein i=1, 2, 3

This calculation shows that a count of X-ray photons counted between an energy threshold $E_{THi}$ to an effective energy $E_i$ is equal to ½ of a count of X-ray photons counted between the effective energy $E_{THi}$ and an effective energy $E_{THi+1}$.

Figure 17:
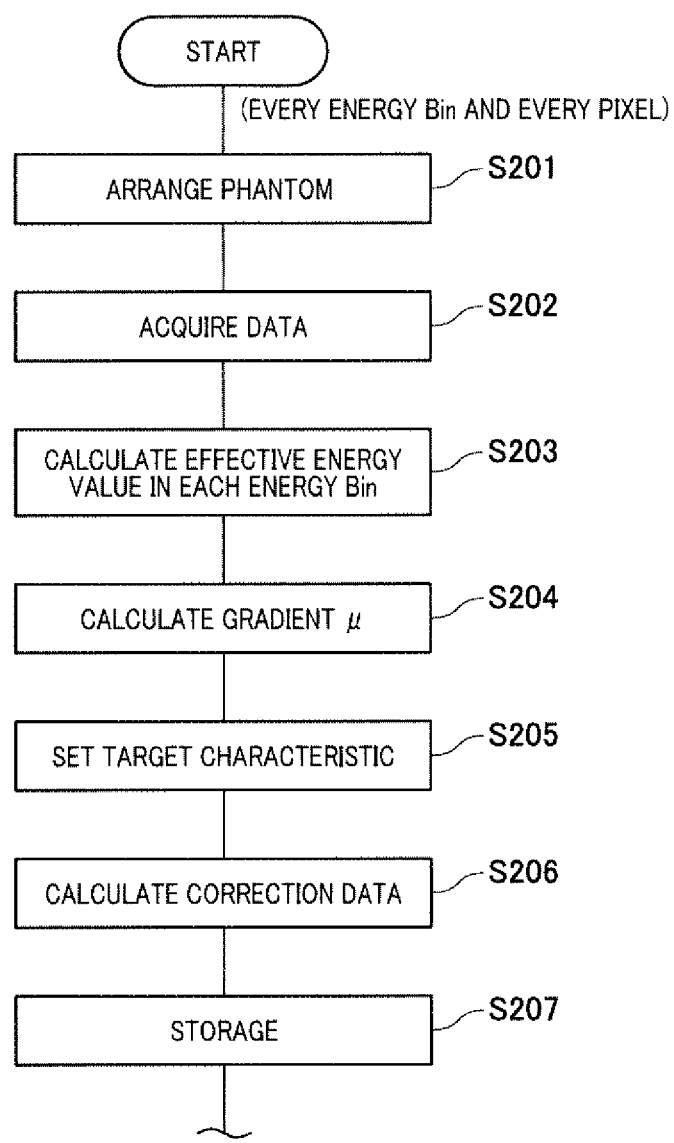
FIG. 17 is a partial flowchart explaining a part of processes performed by a processor, according to the second modification.

In consideration of this fact, a process substantially shown in FIG. 17 is carried out. Specifically, similarly to the foregoing embodiment, in an X-ray energy spectrum of a substance (phantom) imitating an object in view of the linear attenuation coefficients (refer to steps S201 and S202 in FIG. 17), effective energy amounts $E_i$ are calculated based on the foregoing formula (step S203). Values µ (linear attenuation coefficients) each are obtained by multiplying, by a density σ, mass attenuation coefficients (µ/σ: µ is a linear attenuation coefficient; and σ is a density) at the respective effective X-ray energies $E_i$. And, the values µ are employed as gradients in the respective X-ray bins (step S204). The processor 35 then sets, as a target characteristic in each X-ray energy bin, a linear line having a calculated gradient and passing the origin O of the coordinate system, and, based don this target characteristic, calculate correcting data (i.e., calibration data) in each X-ray energy bin (steps S205 and S206). In addition, the calculated correcting data are stored in the first data storage area 33B of the ROM 33 (step S207).

As a result, in the similar way to that shown in FIG. 7, the target characteristic is set at every pixel or at every pixel area composed of a given number of pixels in each of the X-ray energy bins, and the correcting data is produced therefor. This calculation is followed by the process described by step S5 and thereafter in FIG. 10, thereby setting more accurate target characteristics with lesser amounts of calculation, thereby allowing the beam hardening correction in an easier manner.

Alternatively, instead of using the effective energy in each of the X-ray energy bins, a fixed energy value, such as a center of a range defined by the width of each of the energy bins can be adopted to set the target characteristics.

[Third Modification]

A third embodiment relates to a technique for changing a thickness step Δt for acquiring the correcting data, depending on largeness of the thicknesses t provided by a calibration phantom. The reason for this modification is that it is generally required to carry out the beam hardening correction with higher accuracy as the thickness t becomes thinner.

Figure 18:
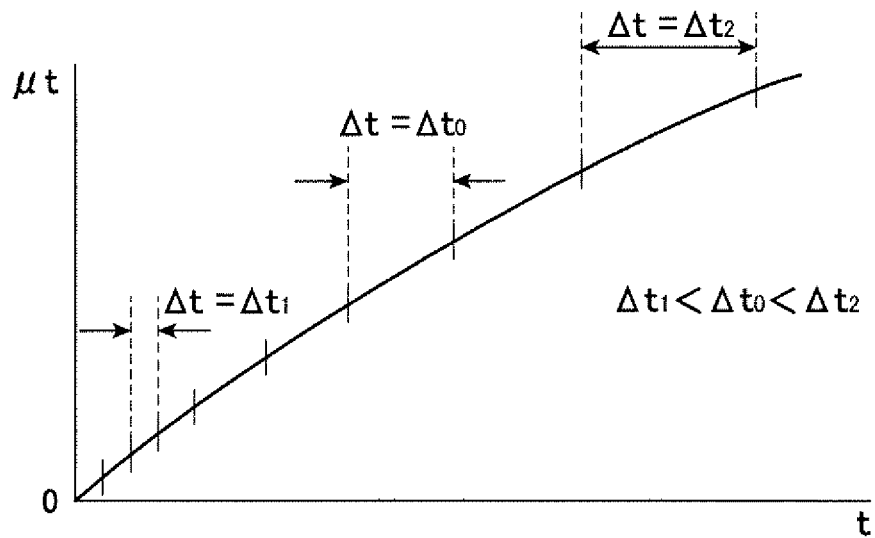
FIG. 18 is a graph explaining an X-ray energy spectrum according to a third modification.

Hence, as pictorially shown in FIG. 18, the thinner the thickness t of a calibration phantom, the smaller the thickness step $\Delta t$ (for example, $\Delta t1<\Delta t2$). Changing and setting the thickness step $\Delta t$ can be carried out by the processor 35 at step S3 shown in FIG. 10 (refer to step S3A). By this, depending on the thicknesses t, the correcting data (multiplication-correcting coefficients $C_i(t)$: i.e., calibration data) can be obtained at every thickness step which is set more finely.

[Fourth Modification]

Figure 19:
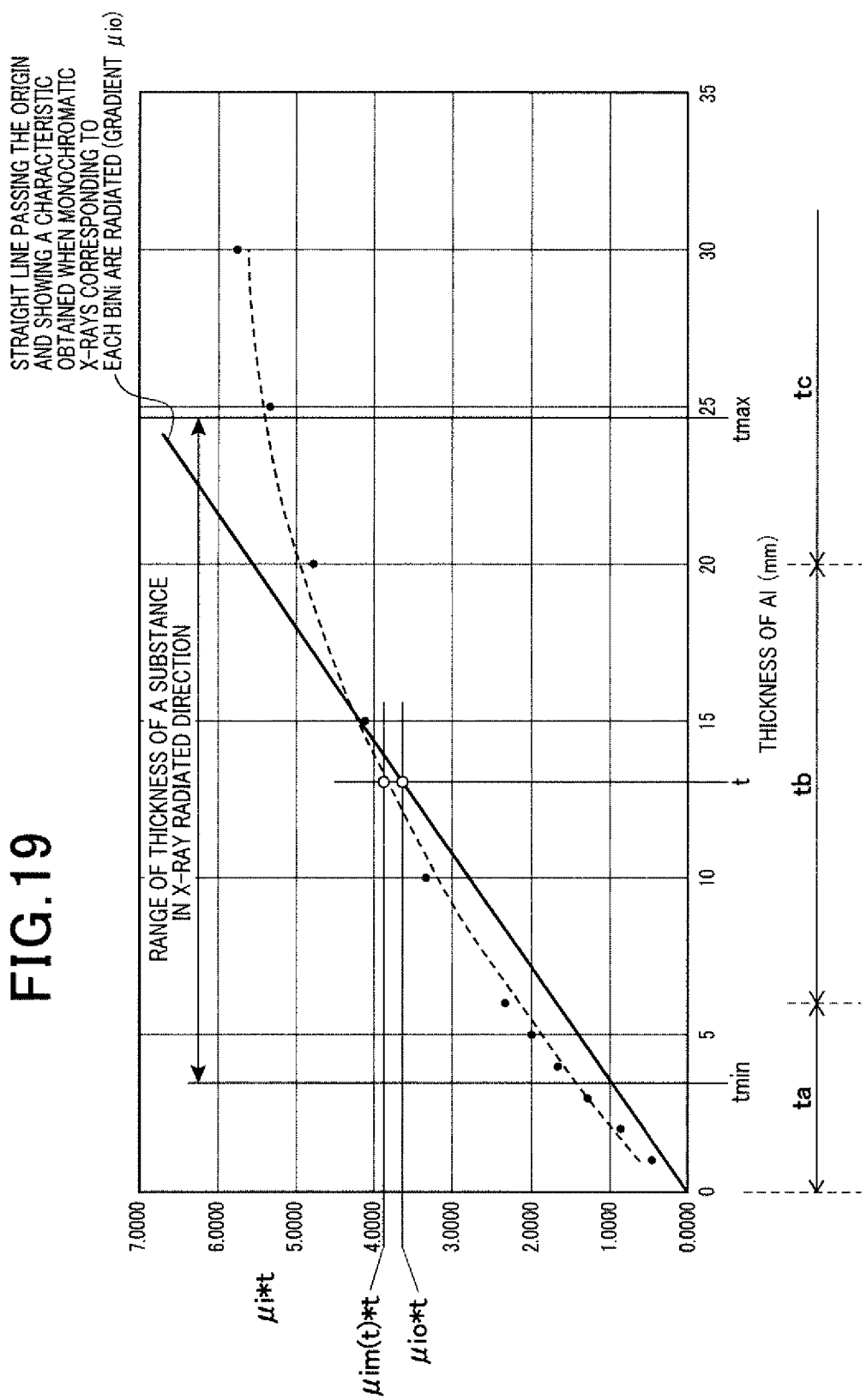
FIG. 19 is a graph explain how to generate correcting data for correcting influence of the beam hardening and other factors, which explains a fourth modification.

In the foregoing embodiment, as shown in FIG. 7, a whole range of the thicknesses t supposedly in size assigned a substance (object) is handled as one thickens section, the characteristic of X-ray attenuation amounts $\mu t$ is approximated by the quadratic function or other functions, and the correcting data is acquired which is for correcting a curve approximated formula to a target characteristic having a gradient $\mu_{io}$. This acquisition can be developed into various other forms. For example, as shown in FIG. 19, the range of thicknesses of an object can be divided into a plurality of sections including for example thinner sections ta, intermediate sections tb, and thicker sections tc, Every section, the foregoing approximation and correcting data generation can be performed.

Figure 20:
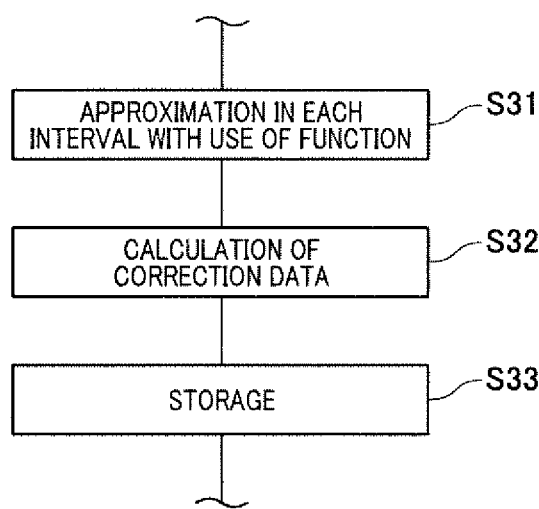
FIG. 20 is a partial flowchart explaining a part of processes performed by the processor, according to the fourth modification.

For such a purpose, at step S3 in FIG. 10, the processor 35 approximates, to functions, X-ray attenuation amounts $\mu t$ measured using a phantom, for every section ta (tb, tc) (step S31), as illustrated in FIG. 20. Then the processor 35 calculates correcting data to correct (or fit) curves shown by the approximation formulae to target characteristics having gradients $\mu_{io}$, for the respective sections ta, tb and tc (step S32). Finally, the processor 35 connects the correcting data in the respective sections into a single set of correcting data, which are then stored in the first data storage area 33B of the ROM 33 (step S33).

As an alternative example, of the three sections ta, tb and tc, any one or two sections can be selected as priority correcting section(s), which is then subjected to the foregoing processing.

In this way, the whole range of thicknesses t of an object or a part thereof is given the correcting data with finer ranges.

[Fifth Modification]

A fifth modification is similar to the second modification in dividing the thicknesses into sub ranges, but different from that in that dividing the sections and calculating correcting data are carried out with shifting in the direction indicating the thicknesses t in the coordinate system.

Figure 21:
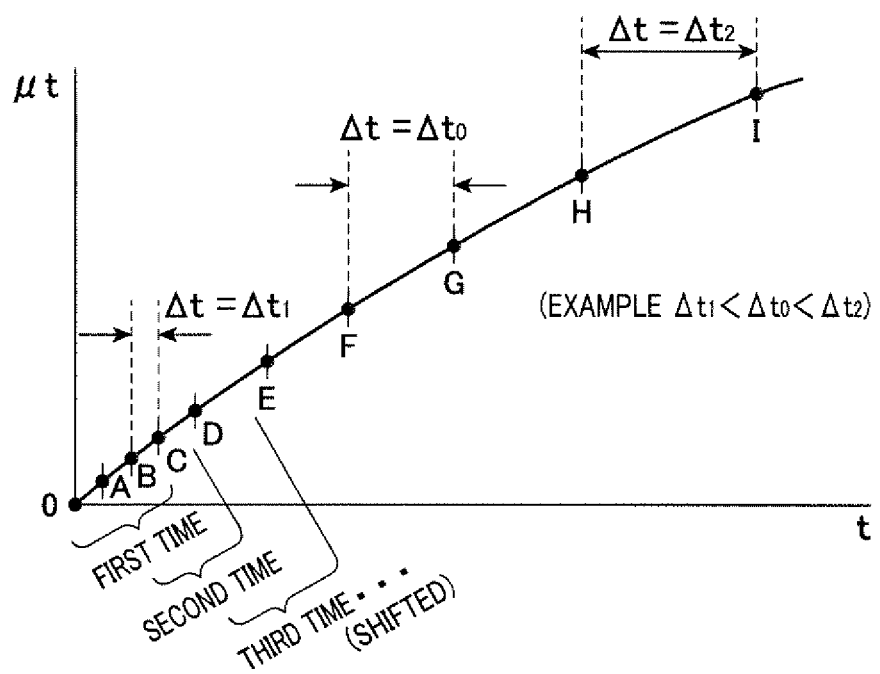
FIG. 21 is a graph of an X-ray energy spectrum explaining how to designate calculation points, which is according to a fifth modification.

Referring to FIG. 21, a technique of the fifth modification will now be described conceptually. A curve shown in FIG. 21 conceptually shows the curve of imaginary attenuation values $\mu_i m(t) \cdot t$, which is measured by using the calibration phantom, which is described with FIG. 19. Firstly, a curve portion passing, for example, three points O (the origin), A and B is approximated by for example a quadratic curve. As to a thickness step $\Delta t$ spaced between the first two points O and A among the three points O, A and B, or a thickness step $\Delta t$ provided by more finely dividing the range spaced between the two points O and A, correcting data is first produced. In this case, the thickness step $\Delta t$ may be variable or fixed in the thickness direction. As the next process, the calculation points are shifted to a thicker side in the thickness t direction, so that a curve portion passing new three points A, B and C is subjected to approximation using for example a quadratic function, and then subjected to generation of correcting data at a thickness step $\Delta t$ derived from the first two points A and B or provided by more finely dividing the space between the two points A and B. then the calculation points are shifted further towards the thicker side in the thicknesses t, which allows the new three points B, C and D to be processed in the same manner. At the fourth cycle and thereafter, the same process as the above is performed repeatedly. In this method, it is possible to widen or fix the width of a section assigned to the calculation points A, B, C, D, . . . , as the thickness t becomes thicker in the thickness direction. Even in the fixed width of the section, the thickness step $\Delta t$ can be set to be larger with increase in the thickness t.

In this modification, the processor 35 performs a process shown in FIG. 19 as a part of the processing at the foregoing steps S3 and S4. Based on preset information, the processor 35 sets a plurality of calculation points O, A, B, C, D, including the origin O (step S310). The processor 35 then designates the first set of three points O, A and B including the origin O (step S311), and calculates or stores correcting data at a thickness step $\Delta t$ provided between the two points O and A or at more finely divided widths between the two points O and A (step S312). Further, the calculation points are shifted, for example, by one point towards a thickness-larger side to designate the next three points A, B and C (step S313). In the same way as the above, correcting data are calculated and stored at the thickness step $\Delta t$ provided between the two points A and B or at more finely divided widths between the two points A and B (step S313). This process is repeated until all the calculation points are completed from being subjected to the calculation (step S315). After this, the processor 35 reads the correcting data for each section and connects them smoothly by using a smoothing process (step S316). Such connected correcting data is again stored in the first data storage area 33B of the ROM 33 (step S317). The processing then proceeds, for instance, to step S5 and thereafter in FIG. 10 described.

In this way, with the calculation points shifted, the correcting data are calculated, thus enabling acquisition of the correcting data in a finer manner as described.

The present invention will not be limited to the configurations stated in the foregoing embodiment and modifications, but may be practiced with various known embodiments within a gist of the present invention.

PARTIAL REFERENCE SIGNS LIST

10 X-ray device
12 data processing apparatus (computer)
21 X-ray tube (acting as part of X-ray generating means)
24 detector
25 data acquisition circuit
33 ROM
33A program storage area
33B first data storage area
33C second data storage area
processor (configuring main part of various processing means: CPU is mounted)
36 image memory (corresponding to part of the image data storing/presenting means)
37 input device
38 display unit (corresponding to par of presenting means)
51 information acquisition unit (corresponding to information acquiring means)
52 pixel data calculation unit (corresponding to pixel data calculating means)
53 image data generation unit (corresponding to image data generating means)

54 image data storing and presenting unit (corresponding to image data storing/presenting means)
P pixel
PA pixel area
OB object

What is claimed is:

1. An X-ray device which inspects an object, wherein beam-shaped X-rays are radiated to the object and the object is inspected based on amounts of the X-rays transmitted through the object, comprising:
   X-ray generating means that generates the X-rays;
   X-ray detecting means that detects transmitted amounts of the X-rays generated by the X-ray generating means and transmitted through the object in each of n-number X-ray energy bins (n is a positive integer of 2 or more) which are set in advance to the X-rays, and outputs detection signals corresponding to the transmitted amounts;
   information acquiring means that acquires, based on the detection signals detected by X-ray detecting means, information showing a thickness t of the object and an average linear attenuation coefficient µ in a transmission direction of fluxes of the X-rays, in each of the energy bins; and
   pixel data calculating means that calculates pixel data composed of pixel values each obtained by multiplying addition information by the thickness t, based on the information acquired by the information acquiring means, the addition information being obtained by mutual addition of the average linear attenuation coefficients µ in the respective energy bins.

2. The X-ray device according to claim 1, wherein the pixel data calculating means is configured to calculate the pixel values based on a formula of:

pixel value=$t \cdot (a1 \cdot \mu1 + a2 \cdot \mu2 + a3 \cdot \mu3)$ wherein a1, a2, and a3·denote weighting coefficients of positive real numbers of 0 or more and the weighting coefficients meet a condition of a1+a2+a3=1.

3. The X-ray device according to claim 2, wherein
   the "n" energy bins consist of three energy bins (n=1, 2, 3) of a low energy bin: Bin 1, a middle energy bin: Bin 2, and a high energy bin: Bin 3 which are provided by dividing the continuous X-ray spectrum depending on energy amounts of the X-rays;
   the information acquiring means is configured to acquire the average linear attenuation coefficients µm the low energy bin: Bin 1, an intermediate energy bin: Bin 2, and a high energy bin: Bin 3, respectively; and
   the pixel data calculating means is configured to calculate the pixel values based on a formula of;

pixel value=$t \cdot (\mu1 + \mu2 + \mu3)/3$ where
   µ1: average liner attenuation coefficient in bin 1,
   µ2: average liner attenuation coefficient in bin 2, and
   µ3: average liner attenuation coefficient in bin 3.

4. The X-ray device according to claim 3, wherein
   the weighing coefficients are changeable and comply with a formula of a condition of $a1+a2+a3=1$.

5. The X-ray device according to claim 1, wherein the X-ray device comprises:
   image data generating means that generates, as image data whose pixel values are the pixel data, data of an average absorption value image; and
   image data storing/presenting means that stores or presents the image data.

6. The X-ray device according to claim 1, wherein
   the information acquiring means is further configured to:
   calculate, at each of pixels, based on the detection signals, vector information associated with attenuation of the X-rays which have been transmitted, the attenuation being caused in the two or more energy ranges; and
   present the vector information,
   wherein
   the vector information is an n-dimensional normalized linear attenuation vector based on a formula of:

$(\mu1, \ldots, \mu n)/{\mu 1}^2 + \ldots + {\mu n}^{2)^{1/2}}$ which is provided when an n-dimensional vector (µ1t, . . . , µnt) is defined by both pi (i=1 to n: n is a positive integer of two or more) indicating an average liner attenuation coefficient in each of the energy bins and t indicating a thickness of the object which is taken along a projected direction of each of the X-rays.

7. The X-ray device according to claim 1, wherein
   the information acquiring means is further configured to:
   calculate, at each of the pixels, based on the detection signals, an absorption vector length associated with attenuation of the X-rays which have been transmitted; and
   present the absorption vector length,
   wherein
   the absorption vector length is a vector length based on a formula of:

$t({\mu 1}^2 + \ldots + {\mu n}^2)^{1/2}$ which is provided when an n-dimensional vector (µ1t, . . . , µnt) is defined by both pi (i=1 to n) indicating an average liner attenuation coefficient in the n X-ray energy bins (n is a positive integer of two or more) and t indicating the thickness of the object which is taken along the projected direction of each of the X-rays.

8. The X-ray device according to claim 1, wherein
   the plurality of X-ray energy bins are two in number and consist of a lower energy bin and a higher energy bin which are provided by dividing the continuous X-ray spectrum depending on amounts of the X-ray energy,
   the information acquiring means is configured to acquire values of the liner attenuation coefficient µ1 (µ2) in each of the lower and higher energy bins, and
   the pixel data calculating means configured to calculate the pixel value based on a formula of:

pixel value=$t \cdot (a1 \cdot \mu1 + a2 \cdot \mu2)/2$ wherein a1 and a2·denote weighting coefficients of positive real numbers of 0 or more and the weighting coefficients meet a condition of a1+a2=2.

9. The X-ray device according to claim 1, wherein
   the number n indicates the number of a plurality of X-ray energy bins and is four or more, and
   the pixel data calculating means is configured to calculate, as the pixel values, based on a formula of:

pixel value=$t \cdot (a1 \cdot \mu1 + \ldots + an \cdot \mu n)/n$ or pixel value=$t \cdot (a1 \cdot \mu1 + \ldots + an \cdot \mu n)/n$ where µ1 to µn denote liner attenuation coefficients in the respective n energy bins, respectively, and a1 to an denote weighing coefficients which are 0 or more positive real numbers and meet a condition of a1+ . . . +an=n.

10. The X-ray device according to claim 7, wherein the information acquiring means is further configured to selectively switch over to one from the other between the average absorption value image and the vector length image and displays the switched image.

11. The X-ray device according to claim 5, wherein the X-ray device comprises an input device with which default values or changed values of the coefficients are inputted, and
wherein the information acquiring means is further configured to calculate the pixel values depending on the default values or the changed values, and display the average absorption value image based on the calculated pixel values.

12. The X-ray device according to claim 1, wherein the X-ray generating means is provided with an X-ray generator generating the beam-formed X-rays having the continuous X-ray spectrum to which the n X-ray energy bins are assigned, and
the X-ray detecting means is provided with a photon counting detector detecting the X-rays which have been transmitted through the object, counts the number of X-ray photons in each of the energy bins as information showing amounts of the transmission, and outputs a counted value of the X-ray photons as the detection signal.

13. The X-ray device according to claim 1, wherein the X-ray generating means is provided with one or more X-ray generators generating the beam-formed X-rays having the continuous X-ray spectrum to which the n X-ray energy bins are assigned, and
the X-ray detecting means is provided with one or more integration-type X-ray detectors detecting the X-rays which have been transmitted through the object and integrates amounts of the transmitted X-rays in each of the energy bins, and outputs an integrated amount of the transmitted X-rays as the detection signal.

14. An X-ray inspection method which inspects an object, wherein beam-shaped X-rays are radiated to the object and the object is inspected based on amounts of the X-rays transmitted through the object, wherein the method comprising:
generating the X-rays;
acquiring a detection signal corresponding to an amount of the X-rays which have been transmitted through the object in each of previously set n-number energy bins of the X-rays (n is a positive integer of two or more);
acquiring, based on the detection signals, information showing a thickness t of the object and an average linear attenuation coefficient $\mu$ in a transmission direction of fluxes of the X-rays, in each of the energy bins; and
calculating pixel data composed of pixel values each obtained by multiplying addition information by the thickness t, based on the acquired information, the addition information being obtained by mutual addition of the average linear attenuation coefficients $\mu$ in the respective energy bins.

15. A data processing apparatus for inspecting an object based on amounts of X-rays transmitted through the object, the apparatus comprising:
X-ray detecting means that detects amounts of the X-rays transmitted through the object in each of n-number X-ray energy bins (n is a positive integer of 2 or more) which are set in advance to the X-rays, and outputs detection signals corresponding to the transmitted amounts;
information acquiring means that acquires, based on the detection signals detected by X-ray detecting means, information showing a thickness t of the object and an average linear attenuation coefficient $\mu$ in a transmission direction of fluxes of the X-rays, in each of the energy bins; and
pixel data calculating means that calculates pixel data composed of pixel values each obtained by multiplying addition information by the thickness t, based on the information acquired by the information acquiring means, the addition information being obtained by mutual addition of the average linear attenuation coefficients $\mu$ in the respective energy bins.

16. A data processing method of inspecting an object based on amounts of X-rays transmitted through the object, the method comprising:
acquiring detection signals corresponding to amounts of the X-rays transmitted through the object in each of n-number X-ray energy bins (n is a positive integer of 2 or more) which are set in advance to the X-rays;
acquiring, based on the detection signals, information showing a thickness t of the object and an average linear attenuation coefficient $\mu$ in a transmission direction of fluxes of the X-rays, in each of the energy bins; and
calculating pixel data composed of pixel values each obtained by multiplying addition information by the thickness t, based on the acquired information, the addition information being obtained by mutual addition of the average linear attenuation coefficients $\mu$ in the respective energy bins.

17. A computer program readably stored in a computer readable non-transient recording medium in advance, the program enabling a computer to read the program and execute steps of the read program for inspecting an object based on amounts of X-rays transmitted through the object, the program enabling the computer to
acquire detection signals corresponding to amounts of the X-rays transmitted through the object in each of n-number X-ray energy bins (n is a positive integer of 2 or more) which are set in advance to the X-rays;
acquire, based on the detection signals, information showing a thickness t of the object and an average linear attenuation coefficient $\mu$ in a transmission direction of fluxes of the X-rays, in each of the energy bins; and
calculate pixel data composed of pixel values each obtained by multiplying addition information by the thickness t, based on the acquired information, the addition information being obtained by mutual addition of the average linear attenuation coefficients $\mu$ in the respective energy bins.

18. The X-ray device according to claim 2, wherein the X-ray device comprises:
image data generating means that generates, as image data whose pixel values are the pixel data, data of an average absorption value image; and
image data storing/presenting means that stores or presents the image data.

19. The X-ray device according to claim 3, wherein the X-ray device comprises:
image data generating means that generates, as image data whose pixel values are the pixel data, data of an average absorption value image; and image data storing/presenting means that stores or presents the image data.

20. The X-ray device according to claim 4, wherein the X-ray device comprises:
 image data generating means that generates, as image data whose pixel values are the pixel data, data of an average absorption value image; and
 image data storing/presenting means that stores or presents the image data.

\* \* \* \* \*